US006185322B1

(12) United States Patent
Ishikawa et al.

(10) Patent No.: US 6,185,322 B1
(45) Date of Patent: Feb. 6, 2001

(54) INSPECTION SYSTEM AND METHOD USING SEPARATE PROCESSORS FOR PROCESSING DIFFERENT INFORMATION REGARDING A WORKPIECE SUCH AS AN ELECTRONIC DEVICE

(75) Inventors: Seiji Ishikawa, Yokohama; Masao Sakata, Ebina; Jun Nakazato, Tokyo; Sadao Shimoyashiro, Fujisawa; Hiroto Nagatomo, Tokyo; Yuzo Taniguchi, Higashimurayama; Osamu Satou, Koganei; Tsutomu Okabe, Kodaira; Yuzaburo Sakamoto, Takasaki; Kimio Muramatsu, Takasaki; Kazuhiko Matsuoka, Takasaki; Taizo Hashimoto, Takasaki; Yuichi Ohyama, Isesaki; Yutaka Ebara, Maebashi; Isao Miyazaki, Isesaki; Shuichi Hanashima, Tokyo, all of (JP)

(73) Assignee: Hitachi, Ltd., Tokyo (JP)

( * ) Notice: Under 35 U.S.C. 154(b), the term of this patent shall be extended for 0 days.

(21) Appl. No.: 08/958,095

(22) Filed: Oct. 27, 1997

Related U.S. Application Data

(63) Continuation of application No. 07/908,550, filed on Jun. 30, 1992, which is a continuation of application No. 07/550,942, filed on Jul. 11, 1990, now abandoned.

(30) Foreign Application Priority Data

Jul. 12, 1989 (JP) .................................................. 1-177934

(51) Int. Cl.⁷ ..................................................... G06K 9/00
(52) U.S. Cl. .............................................. 382/141; 348/86
(58) Field of Search .................................... 382/141–150; 348/86–87, 125–126

(56) References Cited

U.S. PATENT DOCUMENTS 3,751,647   8/1973   Meder et al. .................... 235/151.11
4,817,184   3/1989   Thomason et al. ...................... 382/8

(List continued on next page.)

FOREIGN PATENT DOCUMENTS 56-19635    2/1981   (JP) .
58-165337   8/1983   (JP) .

(List continued on next page.)

OTHER PUBLICATIONS

Semiconductor World 8 [5] 1989, Japan, pp. 118–125.
"IS–2000 Patterned Wafer System Inspection System", by Hitachi, Ltd.
89–67638

Primary Examiner—Bhavesh Mehta
(74) Attorney, Agent, or Firm—Antonelli, Terry, Stout & Kraus, LLP

(57) ABSTRACT

The present invention provides data analysis stations respectively for a probing tester and an automatic particle inspection machine. And, in the data analysis station, the coordinates on which the disposition of the chips are described on a product basis are equal to those on which the locations of the defects are described. Further, the station provides a function of determining which of the chips each defect belongs to. These data analysis stations are connected through a communication line. The present invention is capable of analyzing the data on a chip basis, resulting in being able to grasp the relation between how the defects are caused on each chip and the product character of the chip.

14 Claims, 34 Drawing Sheets

U.S. PATENT DOCUMENTS

| | | | |
|---|---|---|---|
| 4,851,902 | 7/1989 | Tezuka et al. | 382/8 |
| 4,881,863 | 11/1989 | Braginsky | 382/8 |
| 4,894,790 | 1/1990 | Yotsuya et al. | 382/8 |
| 4,928,313 | 5/1990 | Leonard et al. | 382/8 |
| 4,942,618 | 7/1990 | Sumi et al. | 382/8 |
| 4,958,373 | 9/1990 | Usami et al. | 382/8 |
| 5,093,797 | 3/1992 | Yotsuya et al. | 358/101 |
| 5,841,893 * | 11/1998 | Ishikawa et al. | 382/141 |

FOREIGN PATENT DOCUMENTS

| | | |
|---|---|---|
| 59-67638 | 4/1984 | (JP) . |
| 59-228726 | 12/1984 | (JP) . |
| 60-171736 | 9/1985 | (JP) . |
| 62-76712 | 4/1987 | (JP) . |
| 62-220839 | 9/1987 | (JP) . |
| 62-276441 | 12/1987 | (JP) . |
| 63-66446 | 3/1988 | (JP) . |
| 63-66447 | 3/1988 | (JP) . |
| 63-110744 | 5/1988 | (JP) . |
| 63-135848 | 6/1988 | (JP) . |
| 63-220513 | 9/1988 | (JP) . |
| 64-73241 | 3/1989 | (JP) . |
| 1-122132 | 5/1989 | (JP) . |
| 1-137641 | 5/1989 | (JP) . |
| 1-151243 | 6/1989 | (JP) . |

* cited by examiner

FIG. 5A

LOT UNIT DATA TABLE

| PRODUCT NAME (5001) | INSPECTED PROCESS NAME (5002) | LOT NUMBER (5003) | WAFER SIZE (5004) | INSPECTION DATE (5005) | INSPECTION TIME (5006) |
|---|---|---|---|---|---|
| HM001 | A | A01 | 5 | 88/12/01 | 12:45 |
| HM001 | B | A02 | 5 | 89/01/08 | 16:30 |
| HM002 | C | B01 | 6 | 89/02/03 | 17:40 |

FIG. 5B

WAFER UNIT DATA TABLE

| INSPECTED PROCESS NAME (5007) | LOT NUMBER (5008) | WAFER NUMBER (5009) | PARTICLE NUMBER (5010) |
|---|---|---|---|
| A | A01 | 1 | 1 |
| A | A01 | 2 | 10 |
| A | A01 | 3 | 100 |

FIG. 5C

PARTICLE UNIT DATA TABLE

| INSPECTED PROCESS NAME (5011) | LOT NUMBER (5012) | WAFER NUMBER (5013) | PARTICLE COORDINATE X (5014) | PARTICLE COORDINATE Y (5015) | PARTICLE SIZE (5016) |
|---|---|---|---|---|---|
| A | A01 | 1 | 10500 | 10270 | S |
| A | A01 | 2 | 25000 | 8700 | L |
| A | A01 | 2 | 34510 | 28765 | L |

| | 5017 | 5018 | 5019 | 5020 | 5021 | 5022 | 5023 |
|---|---|---|---|---|---|---|---|
| | PRODUCT NAME | WAFER SIZE | CHIP VERTICAL WIDTH | CHIP HORIZONTAL WIDTH | MATRIX VERTICAL WIDTH | MATRIX HORIZONTAL WIDTH | NON-USE CHIP LOCATION |
| | HM001 | 5 | 20000 | 12000 | 5 | 9 | (3,3)(7,3) |
| | HM002 | 6 | 10000 | 8000 | 14 | 17 | (3,3)(4,3) |
| | HM003 | 6 | 10000 | 10000 | 14 | 14 | (3,3)(4,3) |

| 5024 | 5025 |
|---|---|
| PRODUCT NAME | LOT NUMBER |
| HM001 | 20 |
| HM002 | 15 |

FIG. 13

PRODUCT LIST

| No. | PRODUCT NAME | No. | PRODUCT NAME |
|---|---|---|---|
| 1 | HM001 | 2 | HM002 |
| 3 | HL001 | | |
| | | | |
| | | | |
| | | | |
| | | | |
| | | | |
| | | | |
| | | | |
| | | | |

FIG. 14

PROCESS NAME LIST

PRODUCT NAME ( )     REGISTERED PROCESS NUMBER 60

| No. | PROCESS NAME | No. | PROCESS NAME |
|---|---|---|---|
| 21 | | 22 | |
| 23 | | 24 | |
| 25 | | 26 | |
| 27 | | 28 | |
| 29 | | 30 | |
| 31 | | 32 | |
| 33 | | 34 | |
| 35 | | 36 | |
| 37 | | 38 | |
| 39 | | 40 | |

FIG. 15

| | LOT NO. LIST | | |
|---|---|---|---|
| PRODUCT NAME ( ) | PROCESS NAME ( ) | REGISTERED LOT ( ) | |
| No. | LOT NO. | No. | LOT NO. |
| 21 | C45 | 22 | C51001 |
| 23 | C51002 | 24 | C51002 |
| 25 | C51003 | 26 | C51007 |
| 27 | C51008 | 28 | C51009 |
| 29 | C51012 | 30 | C51016 |
| 31 | C51017 | 32 | C51021 |
| 33 | C51023 | 34 | C51027 |
| 35 | C51028 | 36 | C51031 |
| 37 | C51034 | 38 | C51042 |
| 39 | C51044 | 40 | C51045 |

| | WAFER NO. LIST | | |
|---|---|---|---|
| PRODUCT NAME ( ) | PROCESS NAME ( ) | REGISTERED WAFER 25 | |
| No. | WAFER NO. | No. | WAFER NO. |
| 1 | 1 | 2 | 2 |
| 3 | 3 | 4 | 4 |
| 5 | 5 | 6 | 6 |
| 7 | 7 | 8 | 8 |
| 9 | 9 | 10 | 10 |
| 11 | 11 | 12 | 12 |
| 13 | 13 | 14 | 14 |
| 15 | 15 | 16 | 16 |
| 17 | 17 | 18 | 18 |
| 19 | 19 | 20 | 20 |

1047

1048  1049  1050

F I G. 18
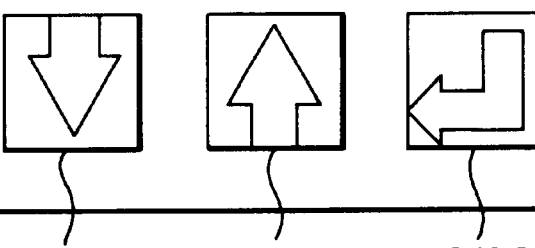

F I G. 20
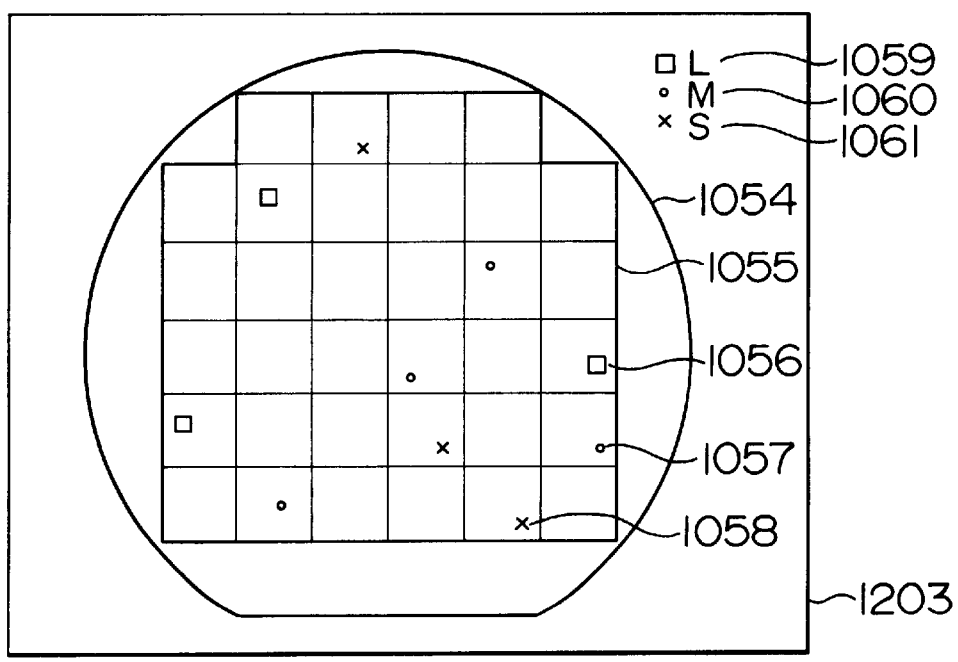
F I G. 21
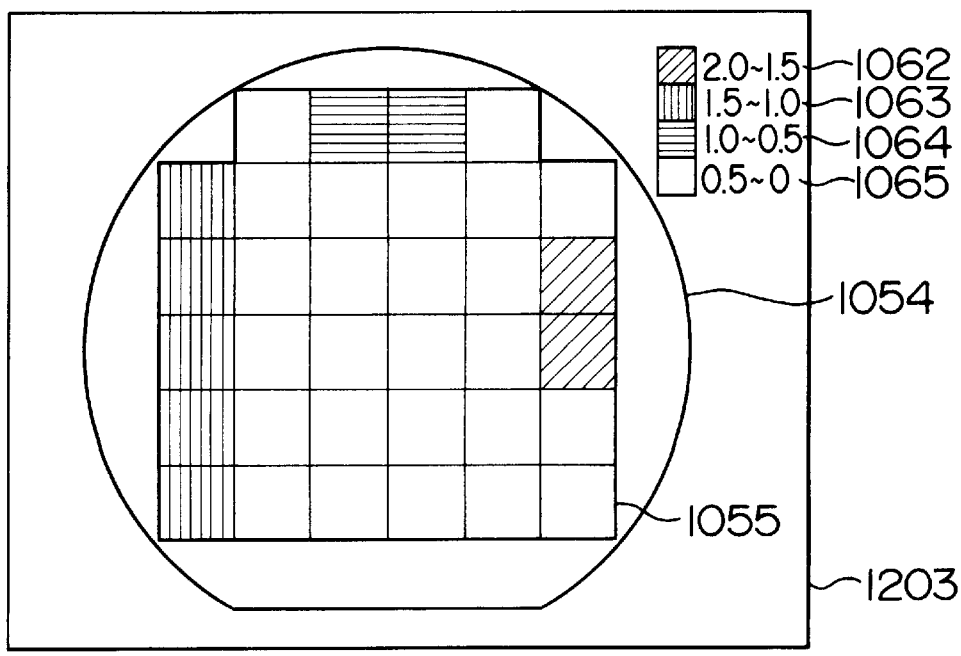

| PRODUCT NAME | CHIP LOCATION X | CHIP LOCATION Y | AREA CATEGORY |
|---|---|---|---|
| HM001 | 1 | 5 | A |
| HM001 | 1 | 6 | A |
| HM001 | 1 | 7 | B |
| HM001 | 1 | 8 | B |
| HM001 | 2 | 5 | C |
| HM001 | 2 | 6 | C |
| HM001 | | | |

| PROCESS NUMBER 5030 | PARTICLE NUMBER 5031 | PARTICLE X COORDINATE 5032 | PARTICLE Y COORDINATE 5033 |
|---|---|---|---|
| 1 | 1 | 5112 | 1022 |
| 1 | 2 | 6811 | 7863 |
| 1 | 3 | 7005 | 12450 |
| 1 | 4 | 9543 | 18635 |
| 1 | 5 | 9611 | 19687 |

FIG. 38A

LOT UNIT DATA TABLE

| PRODUCT NAME (5034) | INSPECTED PROCESS NAME (5035) | LOT NUMBER (5036) | WAFER SIZE (5037) | INSPECTION DATA (5038) | INSPECTION TIME (5039) |
|---|---|---|---|---|---|
| HM001 | A | A01 | 5 | 88/12/01 | 16:40 |
| HM001 | B | A02 | 5 | 89/01/08 | 10:30 |
| HM002 | C | A03 | 6 | 89/02/03 | 11:20 |

FIG. 38B

LOT UNIT DATA TABLE

| INSPECTED PROCESS NAME (5040) | LOT NUMBER (5041) | WAFER NUMBER (5042) | DEFECTS NUMBER (5043) | CRITICAL DEFECTS NUMBER (5044) | DEFECTS CHIP NUMBER (5045) |
|---|---|---|---|---|---|
| A | A01 | 1 | 4 | 3 | 4 |
| A | A01 | 2 | 2 | 1 | 2 |
| A | A01 | 3 | 6 | 2 | 5 |

FIG. 38C

DEFECTS UNIT TABLE

| INSPECTED PROCESS NAME (5046) | LOT NUMBER (5047) | WAFER NUMBER (5048) | DEFECTS COORDINATE X (5049) | DEFECTS COORDINATE Y (5050) | KIND (5051) | CRITI-CALITY (5052) |
|---|---|---|---|---|---|---|
| A | A01 | 1 | 12050 | 14000 | 1 | 1 |
| A | A01 | 1 | 5248 | 18600 | 5 | 0 |
| A | A01 | 1 | 27000 | 17471 | 11 | 0 |

| PRODUCT NAME | WATER NUMBER |
|---|---|
| HM001 | 10 |
| HM002 | 7 |
| HM003 | 16 |

FIG. 48A

PROBING TEST LOT DATA TABLE

| PRODUCT NAME (1146) | LOT NO. (1147) | INSPECTION DATE (1148) | INSPECTION TIME (1149) | OPERATOR NAME (1150) |
|---|---|---|---|---|
| HM001 | A01 | 89/02/05 | 11:10 | SATO |
| HM002 | A02 | 89/02/18 | 10:40 | HASHIMOTO |

FIG. 48B

PROBING TEST WAFER DATA TABLE

| LOT NO. (1151) | WAFER NO. (1152) | CHIP LOCATION X (1153) | CHIP LOCATION Y (1154) | GOOD, DETECTIVES (1155) | WAFER YIELD (1156) |
|---|---|---|---|---|---|
| A01 | 1 | 4 | 6 | 0 | 100.0 |
| A01 | 1 | 11 | 4 | 0 | 100.0 |
| A01 | 2 | 4 | 6 | 0 | 99.0 |
| A01 | 2 | 5 | 8 | 1 | 99.0 |

FIG. 49

| PRODUCT (1157) | ESTIMATED PRODUCT NUMBER (1158) |
|---|---|
| HM001 | 250 |
| HM002 | 150 |
| HM003 | 300 |

F I G. 52
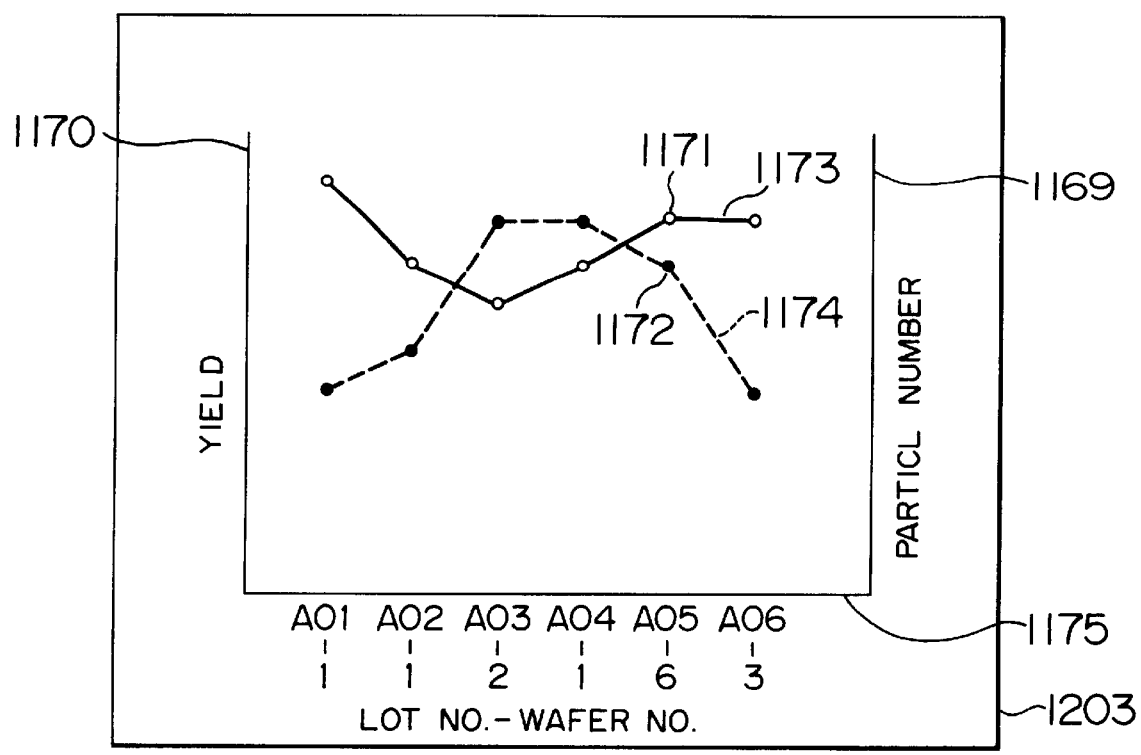

INSPECTION SYSTEM AND METHOD USING SEPARATE PROCESSORS FOR PROCESSING DIFFERENT INFORMATION REGARDING A WORKPIECE SUCH AS AN ELECTRONIC DEVICE

This is a continuation of application Ser. No. 07/908,550, filed Jun. 30, 1992, U.S. Pat. No. 5,847,893; which is a continuation of application Ser. No. 07/550,942, filed Jun. 11, 1990 (now abandoned).

BACKGROUND OF THE INVENTION

The present invention concerns with visual inspection for a product or a part being manufactured and more particularly to an inspection data analyzing system which is capable of inspecting defects or particles on a surface of the product or part and analyzing the inspection data.

In the manufacture of a semiconductor device or the like, product defects often result from particles or defects existing on a surface of a work piece. It is, therefore, necessary to quantitatively inspect particles or defects for normally monitoring if a problem occurs in the manufacturing machine or the circumstance around it. And, it is necessary to grasp how the particles or defects have an adverse effect on a yield and take effective measures for the particles or defects for improving the yield. Hereinafter, the terms "particles or defects" will be generally referred to as "defects".

As an example, the use of an automatic visual inspection machine for data analysis in the manufacture of semiconductors has been disclosed in an article entitled "How does the automatic wafer inspection improve a yield?", Solid State Technology (Japanese Version), July 1988, pages 44 to 48. The visual inspection is carried out for wafers in more than one manufacturing process. Hence, the inspection data includes data for managing the inspection data itself. The managing data contains a product name of a inspected wafer, a lot number, a wafer number, and an inspected process, data, and time, for example. It is necessary to analyze not only the inspection data but also the managing data. The conventional visual inspection machine includes a function of measuring sizes of defects and where the defects are located on a wafer coordinate, a function of measuring the number of defects existing on a wafer, and a means for allowing an operator to determine a category of defects, and the like. The machine inspects the change of the number of defects on each wafer, the distribution of a defects frequency on a wafer-size basis, and the like. Further, the machine serves to analyze the correlation between the number of defects on each wafer (defects density) and the yield of the wafer as well.

And, each wafer has to be identified in more than one visual inspection process in the data analysis. Conventionally, the operator has visually recognized a wafer number. To reduce the burden of this operation, an automatic particle inspection machine having a means for automatic recognition of a wafer number has been disclosed in JP-A-63-213352.

The known automatic visual inspection machine has been categorized into two groups. One is referred to as an automatic particle inspection machine which is an inspection machine employing a light-scattering system. This machine serves to inspect particles existing on a wafer. It is thus unable to always inspect defects. The other group is an inspection machine employing a pattern recognition system. It is referred to as an automatic visual inspection machine or an automatic defect inspection machine, which has a function of recognizing defects in addition to particles. The automatic visual inspection machine needs about 1000 times as long an inspection time as the automatic defect inspection machine. The former machine can thus inspect a far smaller number of wafers than the latter. For monitoring how defects are caused in a mass production line, the two methods are provided. The first method is to restrict the processes to be visually inspected to a specific process (Solid State Technology (Japanese Version), July 1988, pages 44 to 48). The second method is to take the steps of matching the particle inspection data to the visual inspection data over all the processes and machines, checking the correlation between particles and defects, and presuming how defects are caused on the particle inspection data (Semiconductor World, May 1989, pages 118 to 125). Further, in analyzing data, these methods require an operator who serves to analyze data, because there exist lot of data and various kinds of data analysis methods in analyzing data.

The conventional methods is uncapable of grasping how defects are caused on each chip. Hence, they can merely perform correlation analysis between the number of defects per wafer and a yield. That is, these methods have a disadvantage that they cannot grasp the relation between defects per wafer and a product character. In addition, one semiconductor for one wafer is provided at this time, while two or more semicondcutors for one wafer will be provided in future. It is necessary to enhance the data processing unit from a wafer unit to a chip-unit basis. The new data analysis technique is expected accordingly.

And, for inspecting how many defects are caused in a mass production line, the foregoing first method is designed to determine the process to be visually inspected on the basis of the knowledge of an operator and the result of a probing test. The foregoing second method requires large labor for matching the particle inspection data to the visual inspection data over all the processes and machines.

Moreover, an operator who is mainly in charge of maintaining and managing the manufacturing machine does not have a spare time to analyze the inspection data of a wafer given by his or her machine. Hence, the operator requests the data analysis of another operator who is mainly in charge of it. However, novel data analysis method and means are expected which anyone can operate easily and quickly and which serve to output the analyzed data.

SUMMARY OF THE INVENTION

It is therefore an object of the present invention to provide an inspection data analysis system which is capable of analyzing data per chip for the purpose of grasping the relation between the occurrence condition of defects per chip and the product character of each chip.

And, it is a further object of the present invention to provide an inspection data analyzing system which is capable of easily determining a manufacturing process which causes problems and the contents of the problems.

It is another object of the present invention to provide an inspection data analyzing system which is capable of monitoring the overall production line and efficiently inspecting the quantity of caused defects in a mass production line.

To achieve the foregoing objects, the present invention offers a probing tester, an automatic particle inspection machine, and an automatic visual inspection machine respectively having data analysis stations. Each data analysis station has chip arrangement information for each product and serves to describe the locations of defects on the coordinate system on which the chip disposition is described. And, the station provides a function for determining which chip each defect is caused. These data analysis stations are linked with a communication line.

Further, for inspecting the quantity of caused defects in the mass production line, the particle inspection machine operated at a higher inspection speed employs the step of monitoring the overall manufacturing line, inspecting the portions around caused defects, and monitoring the quantity of caused defects.

And, in order for anyone to use the machine, the data analysis station is designed to offer a routine data retrieval method, a routine operation method, and a routine analysis result output format.

As mentioned above, each data analysis station provides chip disposition information, a function of describing the locations of caused defects on the coordinate system on which the chip disposition is described, and a function of determining which chip each defect is caused. It is thus possible to grasp how particles are attached and defects are caused on each chip. By linking these data analysis stations with a communication line, therefore, the data analysis station for probing test data sends the probing data to the station for particles and defects data so that the latter station can inspect the relation between the condition of caused defects on each chip and the probing test result (product character). As will be understood from the above description, the present invention is designed so that the particle inspection machine operating at a higher inspection speed serves to monitor the overall manufacturing line and the visual inspection machine serves to inspect portions around caused particles for inspecting the quantity of caused defects. Hence, this invention is capable of efficiently inspecting the quantity of caused defects in a mass production line.

Further, in analyzing data, as mentioned above, this invention has a routine data retrieval method, a routine operating method, and a routine output format, so that anyone can analyze the data and obtain clear outputs.

BRIEF DESCRIPTION OF THE DRAWINGS

FIG. 5A is a chart showing a data table for each lot in a particle database;

FIG. 5B is a chart showing a data table for each wafer in the particle database;

FIG. 5C is a chart showing a data table for each particle in the particle database;

FIGS. 13 to 18 are views respectively showing a list of each data;

FIG. 20 is a view showing a particle map;

FIG. 21 is a view showing a map about how particles are attached on chips;

FIG. 38A is a chart showing a data table for each lot in the defects database shown in FIG. 37;

FIG. 38B is a chart showing a data table for each wafer in the defects database shown in FIG. 37;

FIG. 38C is a chart showing a data table for each defect in the defects database shown in FIG. 37;

FIG. 48A is a chart showing a probing test lot data table in a probing test database shown in FIG. 46;

FIG. 48B is a chart showing a probing test wafer data table in the probing test database shown in FIG. 46;

FIG. 49 is a chart showing an analysis data auxiliary file;

FIG. 52 is a chart showing an overlay trend between the particle number and the yield;

DESCRIPTION OF THE PREFERRED EMBODIMENTS

Embodiment 1

Figure 1:
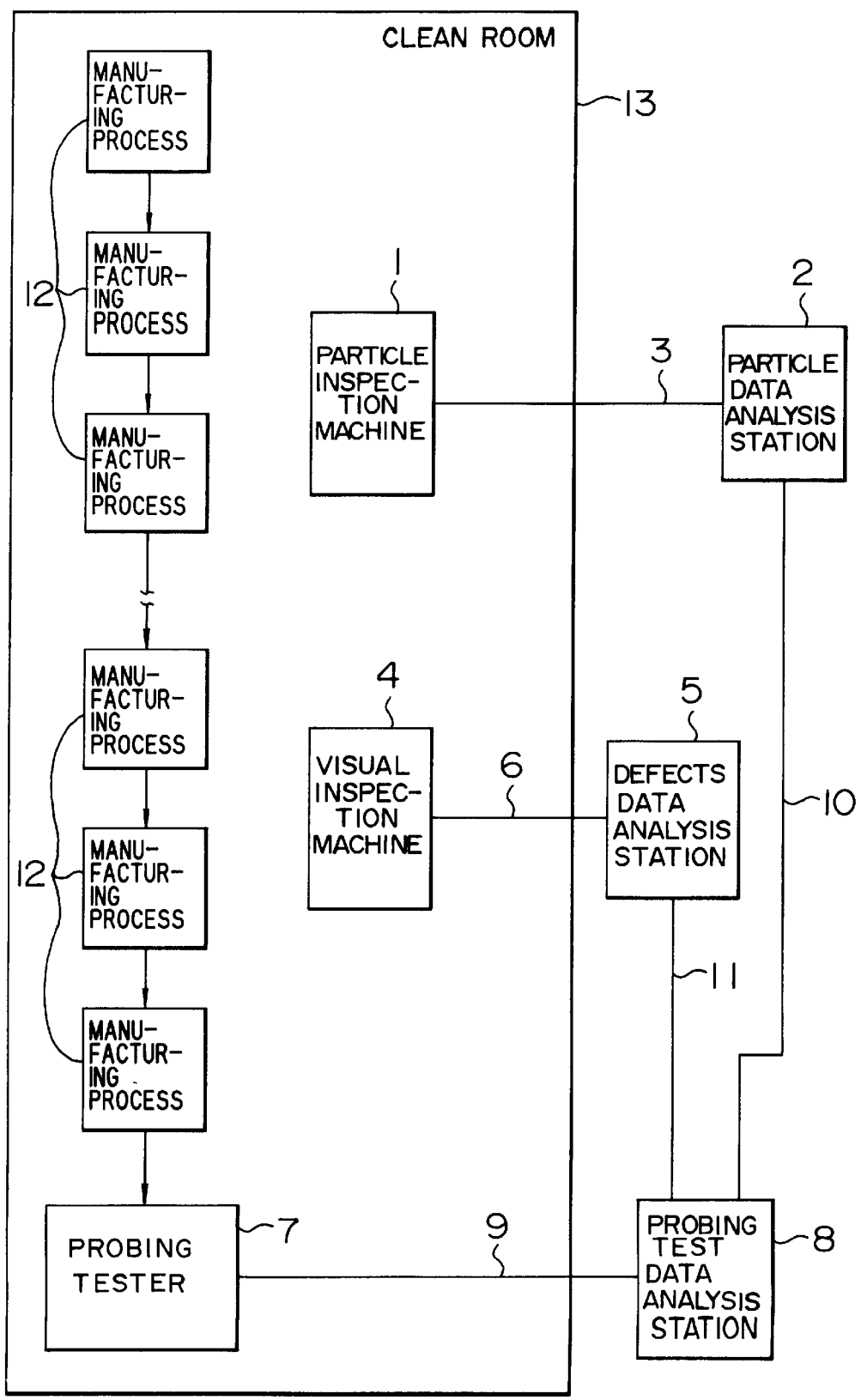
FIG. 1 is a diagram showing overall arrangement of an inspection data analysis system according to an embodiment of the present invention.

The overall arrangement of the embodiment will be described with reference to FIG. 1. This embodiment is a manufacturing line for semiconductor devices to which the present invention is applied. 12 denotes a semiconductor device manufacturing process. It is normally located in a clean room 13 in which the circumstance is kept clean. In the clean room 13, there are provided a particle inspection machine 1 having a function of measuring the number of defects existing on a product wafer and the locations of the defects on a wafer coordinate system, a visual inspection machine 4 having functions of measuring the number of defects existing on a product wafer and the locations of the defects on the wafer coordinate system and of recognizing a category of defects (the visual inspection machine 4 simply referred hereinafter indicates this inspection machine. This inspection machine serves to inspect general defects such as pattern defects, particles, and discoloration defects.), and a probing tester 7 for testing the product character of a chip. These machines are disclosed in Kubota et. al.; "Particle and Visual Inspection Machines", Hitach Critique, 71 volumes, No. 5, pages 55 to 62, for example. The particle inspection machine 1, the visual inspection machine 4, and the probing tester 7 respectively provide a particle data analysis station 2, a defects data analysis station 5, and a probing test data analysis station 8, which are all installed outside of the clean room 13. The inspection machines 1, 4, 7 are linked with the analysis stations 2, 5, 8 through communication lines 3, 6, 9. Further, the particle analysis station 2 is linked with the probing test data analysis station 8 through a communication line 10 and the defects analysis station 5 is linked with the probing test data analysis station 8 through a communication line 11.

On the semiconductor device manufacturing line, wafers flow on a lot basis. For particle- or visual-inspecting these wafers, after finishing the process to be particle- or visual-inspected, each lot is carried to the particle inspection machine 1 or the visual inspection machine 4 in which some or all wafers contained in the lot are inspected. For carrying out the particle or visual inspection, it is possible to employ a method for determining a subject process on the basis of the operator's knowledge or a method for determining a process to be viaually inspected on the basis of the particle-inspecting result as mentioned below. In the particle or visual inspection, data is supplied to each inspection machine. The data contains a lot number of a wafer, a wafer number, an inspection day and time, a process located immediately before the inspection, and the like. The process-completed wafers are carried to the probing tester 7 at each lot, in which tester 7 all the wafers contained in the lot are subject to a probing test. Herein, the lot number of a wafer, the wafer number, and the inspection day and time are supplied to the probing tester 7. The particle data analysis station 2 and the defects data analysis station 5 contain information about how chips are disposed on a wafer for each product. Based on the information, these stations serve to determine which chip the inspected defects belong to on the basis of the locations of the inspected defects placed on the chip coordinate system and count how many defects are brought about on each chip. Based on the number of defects existing on a wafer, the location coordinates of the defects, and the number of defects on a chip, the particle inspection data analysis station 2 and the visual inspection data analysis station 5 serve to carry out the analysis described in each of the embodiments 3, 4, 5, 6, 7, 8, 9, 10, 11, 15, 16, 17, 18, 19, 20, 21, 22, 23, 24, and 25. Further, the particle inspection data analysis station 2 and the visual inspection data analysis station 5 serve to carry out the analysis described in each of the embodiments 28, 29, 30, 31, 32, 33, 34, 35, 36, and 37 on the basis of the number of defects existing on a wafer, the location coordinates of defects, the number of defects on a chip, and the data about a product character read from the probing test data analysis station 8.

Embodiment 2

Figure 2:
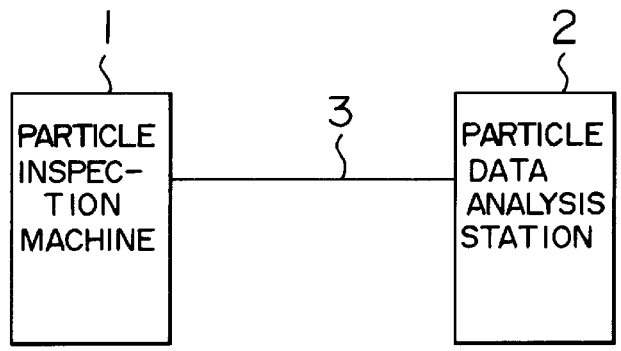
FIG. 2 is a diagram showing partial arrangement of a particle inspection system shown in FIG. 1.

In this embodiment, the description will be described to the arrnagement of the particle inspection machine 1 and the particle inspection data analysis station 2 included in the inspection data analysis system described in the embodiment 1 with reference to FIG. 2.

The present system consists of the particle inspection machine 1 for inspecting particles on a wafer and the particle data analysis station 2 for analyzing data sent from the particle inspection machine 1. The former machine 1 is connected to the latter station 2 with a communication line 3.

Figure 3:
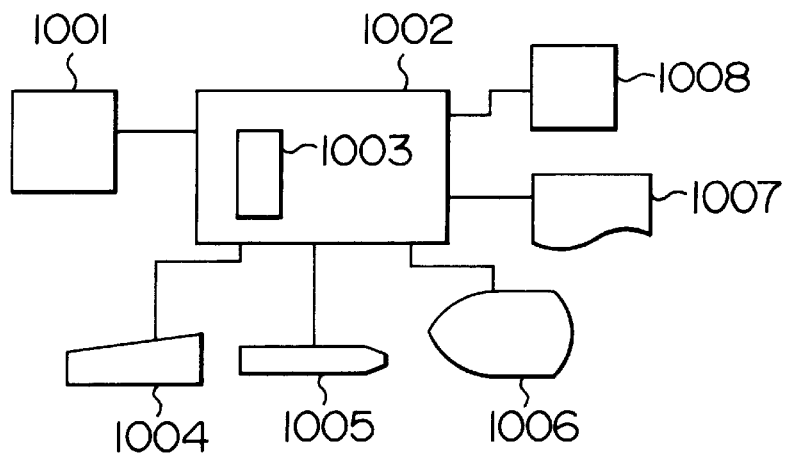
FIG. 3 is a diagram showing arrangement of a particle inspection machine shown in FIG. 2.

FIG. 3 illustrates the arrangement of the particle inspection machine 1. The particle inspection machine 1 comprises a particle sensor 1001, a particle sensing signal processing unit 1002, a memory 1003, a keyboard 1004 served as an input unit, a bar-code reader 1005, a CRT 1006 and a printer 1007, both of which are served as an output unit, and an external communication unit 1008 for carrying out the communication with the particle data analysis station 2. The machine 1 has a function of defining the two-dimensional location coordiantes of particles to be inspected on a wafer, the sizes of the particles, and the number of particles existing on the wafer.

Figure 4:
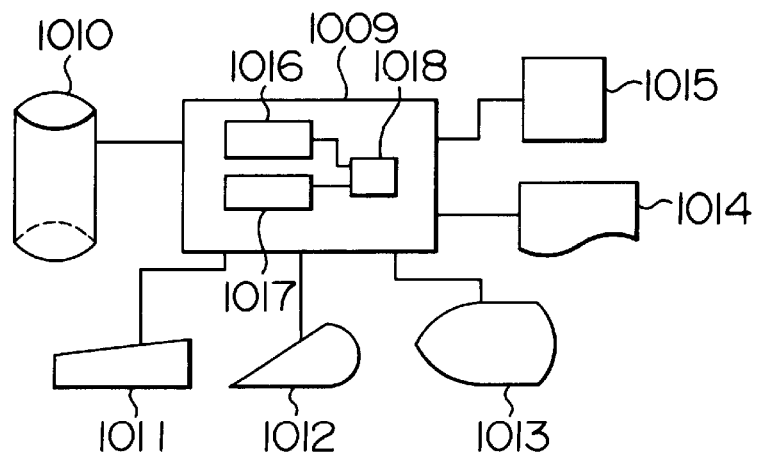
FIG. 4 is a diagram showing a particle data analysis station shown in FIG. 2.

FIG. 4 illustrates the arrangement of the particle data analysis station 2. The particle data analysis station 2 comprises a particle data processing unit 1009, a particle database 1010 for saving the inspection data sent from the particle inspection machine 1, a keyboard 1011 served as an input processing unit, a mouse 1012, a CRT 1013 and a printer 1014 served as an output unit, an external communication unit 1015 for carrying out communication with the particle inspection machine, a memory 1016 located inside of the particle data processing unit, an internal harddisk 1017, and a CPU 1018.

In wafer inspection, the particle management data is supplied to the particle inspection machine 1 using the keyboard 1004 or the bar-code reader 1005. The data contains an inspected wafer name, an inspected process name, a lot number, a wafer number, an inspection data, an inspection time, and an operator. Further, the particle inspection data is also saved together with the particle management data. This particle inspection data contains the number of the particles existing on the inspected wafer, the location coordinates of the particles, and the sizes of the particles, which are measured in the particle inspection machine 1. Each particle can be categorized in L, M, and S sizes in larger order when saved.

The form of the particle database 1010 is illustrated and described with reference to FIG. 5. The particle database 1010 includes three databases referred to as a lot unit data table (see FIG. 5A), a wafer unit data table (see FIG. 5B), and a particle unit data table (see FIG. 5C). The lot unit data table serves to save particle management data 5001, 5002, 5003, 5005, 5006 and a wafer size 5004. The wafer unit data table serves to save a lot number 5008, a wafer number 5009, and the number of particles 5010 existing on the inspected wafer contained in the particle inspection data. The particle data processing unit 1009 saves a map information file and a lot number management file for each product in the internal harddisk 1017. The map information file contains a wafer size for each product, a chip vertical width 1019, a chip horizontal width 1020, a matrix vertical width 1022, a matrix horizontal width 1023, and non-use chip positions 1024, 1025 registered therein. The lot number management file for each product contains a lot number 5025 for each product registered therein. The formats of the map information files will be illustrated with reference to FIG. 7. The format of the lot number management file for each product will be illustrated with reference to FIG. 8.

Figure 10:
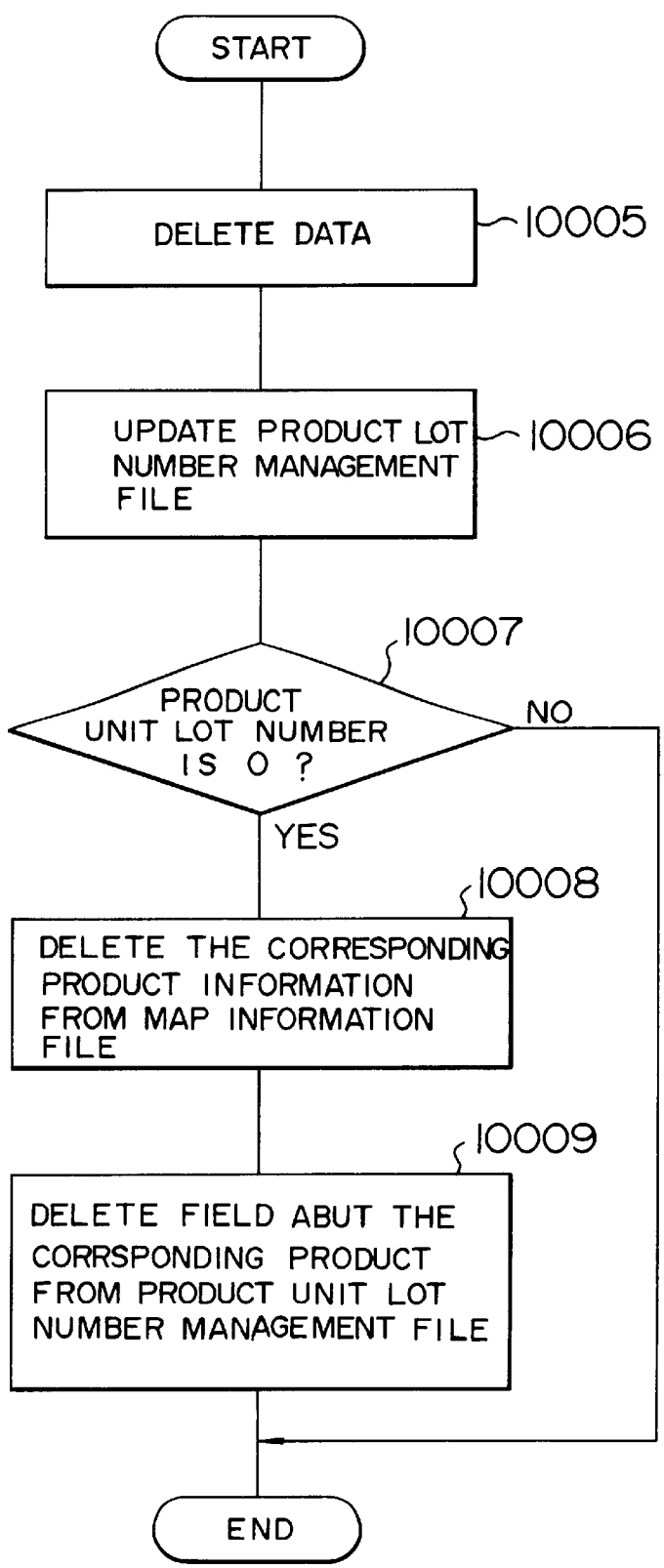
FIG. 10 is a flowchart showing the procedure involved with deletion of data.

Next, how to register the data will be described with reference to FIG. 9. After the particle inspection machine 1 finishes the inspection of one lot (step 10001), it sends the particle management data and the particle inspection data to teh aprticle data analysis station 2 through the communication line 3 (step 10002). When the particle management data and the particle inspection data for one lot are rejected in the particle database 1010 (step 10003), the particle data processing unit 1009 increments by one the lot number for each product in the lot number management file for each product (step 10004). Then, the data deletion procedure is illustrated in FIG. 10. An analysis operator routinely maintains the particle database 1010 and deletes the data about the lot he or she determines unncessary (step 10005). When the one-lot data is deleted from the particle database 1010, the particle data processing unit 1009 decrements by one the lot number for each product in the lot number management file for each product (step 10006). Then, in the product unit lot number management file, it is determined if the product unit lot nubmer is zero (step 10007). If yes, the map information file about the product is deleted and then the file about the product in the product unit lot number management file is deleted (step 10008). If no at the step 10007, the procedure is directly finished.

Embodiment 3

Figure 11:
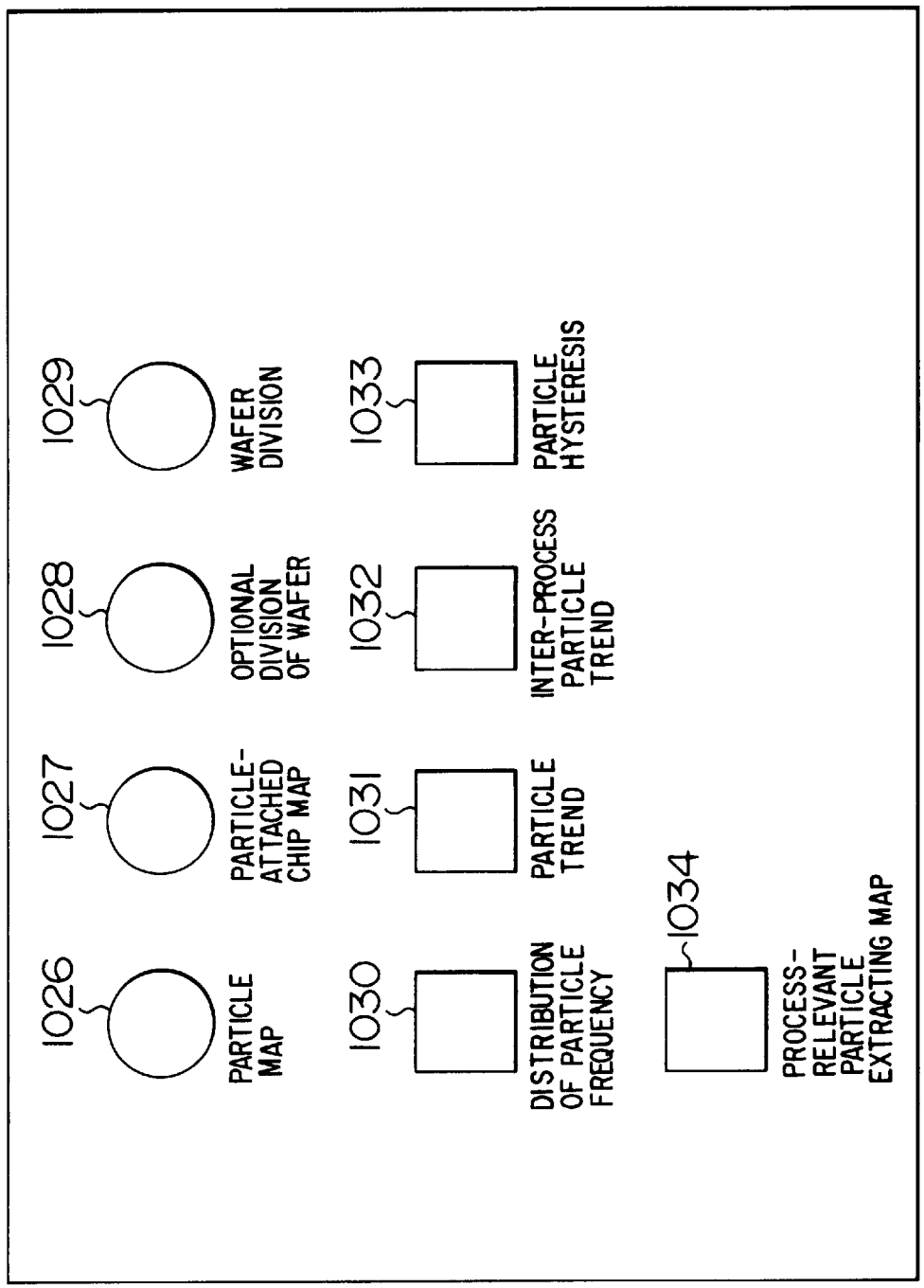
FIG. 11 is a view showing an initial screen.
Figure 12:
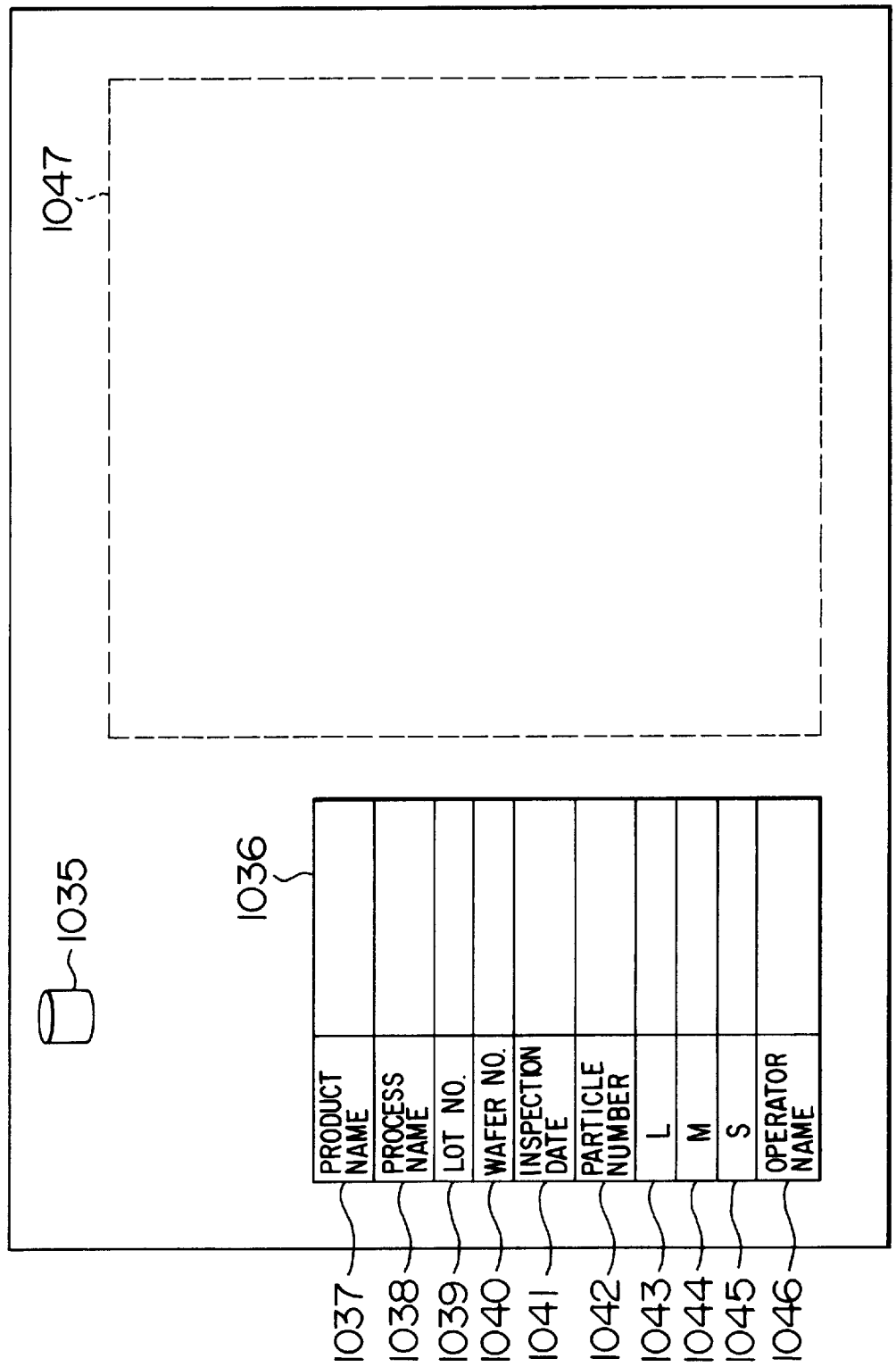
FIG. 12 is a view showing a retrieval screen.
Figure 17:
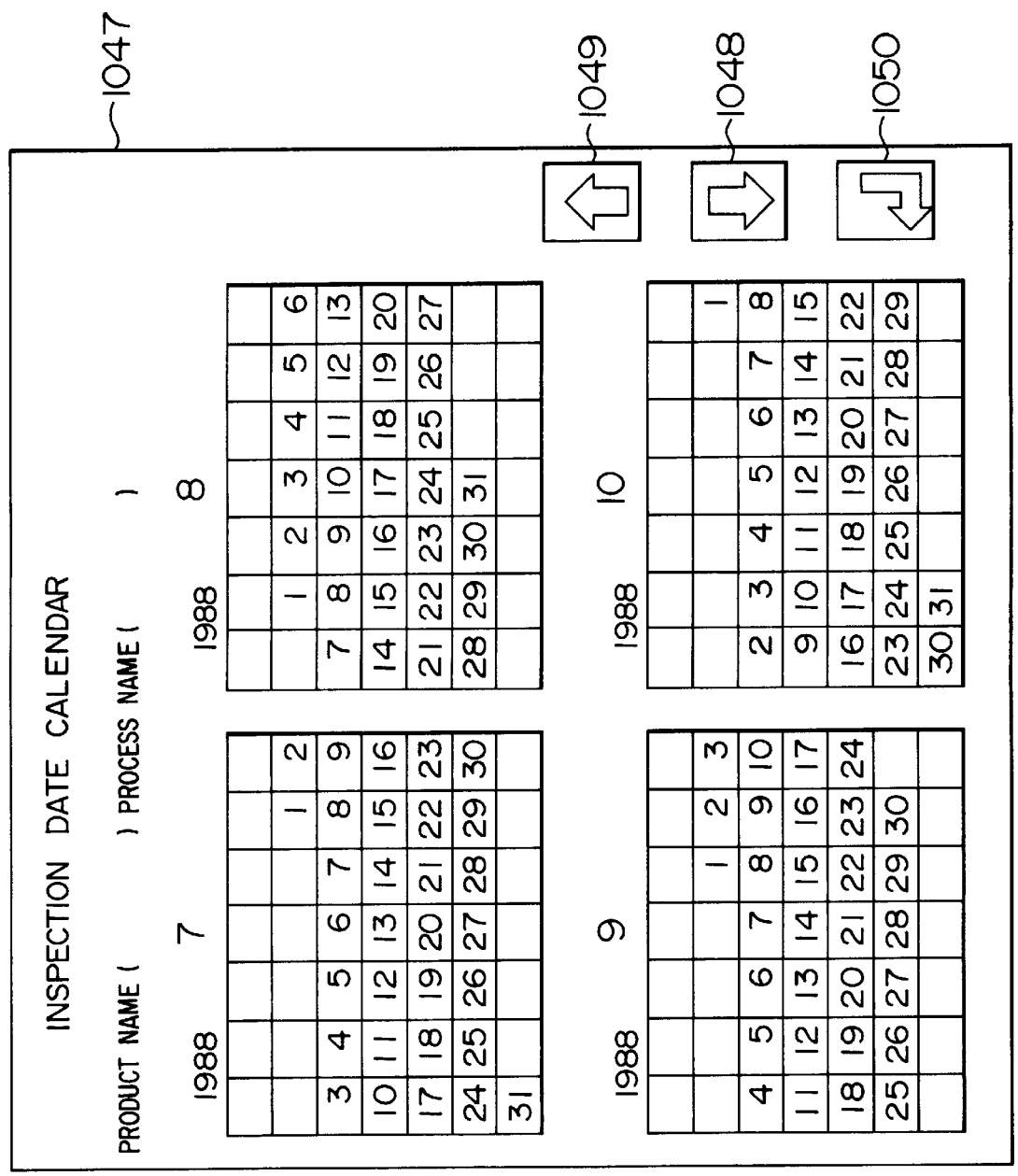

This is an embodiment concerning how to use the particle data analysis station 2 described in the embodiment 2. In the initial screen shown in FIG. 11, several analysis function icons (1026 to 1034) are rovided. These icons include analysis functions to be described later with respect to the embodiments 4 to 12. An analysis operator selects a desired analysis function icon and then specifies a retrieval condition on a retrieval screen shown in FIG. 12. For specification, one or more items are specified by the mouse 1012 shown in FIG. 4 and then a finish icon 1050 is specified. This retrieval screen comprises a basic data display column 1036 at the lower-left portion of the screen, a database retrieval icon 1036 at the upper-left portion, and a display section 1047 at the central to the right portion, the display section containing a product list, a process list, a lot number list, a wafer number list, an inspection date calendar, and an operator name list. The basic data display column 1036 contains a product name 1037, a process name 1038, a lot number 1039, a wafer number 1040, an inspection date 1041, a particle sum 1042, an L-sized particle number 1043, an M-sized particle number 1044, an S-sized particle number 1045, and an operator name 1046. For specifying the retrieval condition, it is necessary to specify the product name 1037. It is possible to specify the process name 1038, the lot number 1039, the wafer number 1040, the inspection date 1041, and the operator name 1046 if necessary. The specified results are displayed on the basic data display column 1036. By specifying the product name item 1037 on the initial screen by the mouse 1012, the product name list shown in FIG. 13 is displayed on the display section 1047. The displayed list includes all the product names 5001 registered in the database 1010. Further, in FIG. 13, 1048 denotes a lower scroll icon, 1049 denotes an upper scroll icon, and 1050 denotes a finish icon. When the analysis operator specified one desired product name of the list with the mouse 1012, the specified product name is displayed in the product name item 1037. Next, when the analysis operator specifies the process name in the item 1038 with the mouse 1012, the process name list shown in FIG. 14 is displayed on the display section 1047. This displayed process name list contains only the process name 5002 about the specified product names in the data registered in the database 1010. The analysis operator specifies a desired process name in the process name list with the mouse 1012. Then, when he or she specifies the lot number item 1039 with the mouse 1012, the lot number list is displayed as shown in FIG. 15. This lot number list contains only the lot number 5003 about the specified product name and process name in the data registered in the database 1010. The analysis operator specifies a desired lot number from among the lot number list with the mouse 1012. Then, when the operator specifies the wafer number item 1040 with the mouse 1012, the wafer number list is displayed as shown in FIG. 16. This wafer number list contains only the wafer number 5009 about the product name 50001, the process name 5002, and the lot number 5003, which are all specified, in the data registered in the database 1010. The analysis operator specifies a desired wafer number from among the wafer number list with the mouse 1012. Next, when he or she specifies the inspection date item 1041 with the mouse 1012, an inspection date calendar is displayed as shown in FIG. 17. The inspection date calendar indicates the earliest to the latest month of inspection date 5005 about the product name, the process name, the lot number, and the wafer number, which are all specified, in the data registered in the database 1010. The analysis operator specifies a desired period by specifying the earlier date and the latest date in the inspection date calendar with the mouse 1012. Next, when the operator specifies the operator name item 1046 with the mouse 1012, the operator name list is displayed as shown in FIG. 18. The operator name list contains only the operator names about the product name, the process name, the lot number, the wafer number, and the inspection date, which are all specified, in the data registered in the database 1010. The analysis operator specifies a desired operator name from among the operator name list with the mouse 1012. After the desired item, an analysis operator specifies the database retrieval icon. The particle data analysis station 2 serves to retrieve the satisfactory data about the product name, the process name, the lot number, the wafer number, the inspection date, and the operator name from the particle database 1010 and send it to the particle data processing unit 1009. If no item is specified, the particle data analysis station 2 serves to retrieve all the satisfactory data about the other specified items from the particle database 1010 and send it to the particle data processing unit 1009.

Figure 19:
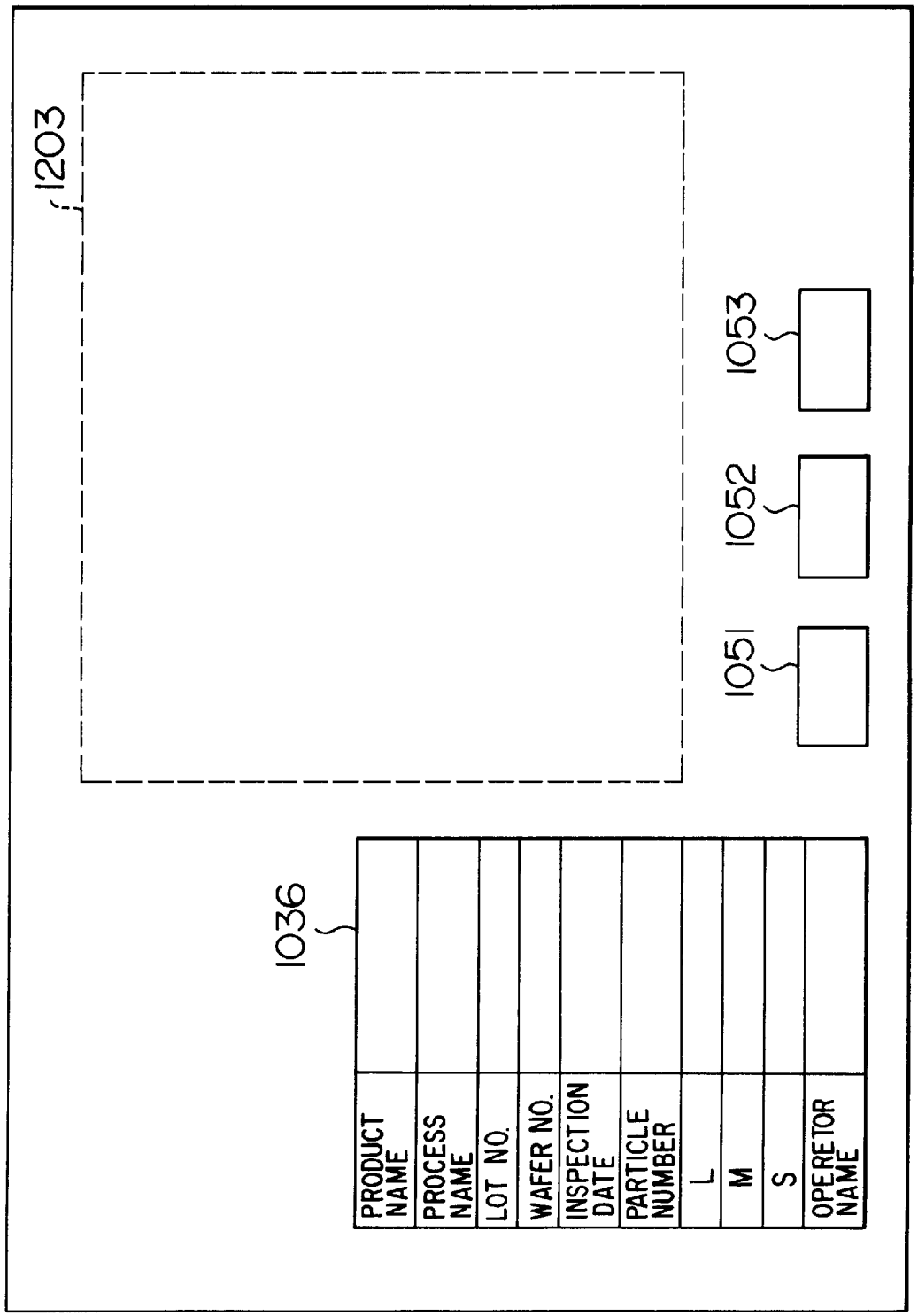
FIG. 19 is a view showing an analysis screen.

When the particle data processing unit 1009 finishes reading of the data, the analysis screen is displayed as shown in FIG. 19. Three operation icons 1051, 1052, 1053 are provided in the lower-central to the lower-right portion of the screen. The basic data display column 1036 is provided in the lower-left portion of the screen. On the central portion is output the analysis result. This basic data display column 1036 on the screen is identical to the basic data display column 1036 on the initial screen shown in FIG. 12. These operation icons serve as a mode change 1051, a hard-copy 1052, and a finish 1053. The mode change icon 1051 is used for changing the analysis mode. The hard-copy icon 1052 is used for printing the screen displayed on the CRT 1013 on the printer 1014. The finish icon 1053 is used for finishing the analysis and returning the screen to the initial screen.

Embodiment 4

Next, the description will be directed to an embodiment about the analysis with reference to FIG. 20. This embodiment is referred to as a particle map.

With respect to the present embodiment, how particles are distributed on a wafer is displayed on the basis of the information measured in the particle inspection machine 1.

The analysis operator has to specify a product name. Further, he or she may specify a process name, a lot number, a wafer number, an inspection date, and an operator name if necessary. By specification, the particle database 1010 sends the information about the particle location coordiantes and the particle diameters to the memory 1016.

The output depicts an outer circle 1054 of a wafer and indicates particle locations by marks. It may over-depict a border line 1055 of the chip at this time. And, three size kinds of particles 1059, 1060, 1061 have respective display colors or marks. When the mode change icon 1051 is specified, at each specification time, it is possible to selectively represent L-, M-, and S-sized particles. Further, it is also possible to concurrently specify more than one wafer and display all of the particle distributions on the CRT 1013 in an overlapped manner.

Embodiment 5

Figure 22:
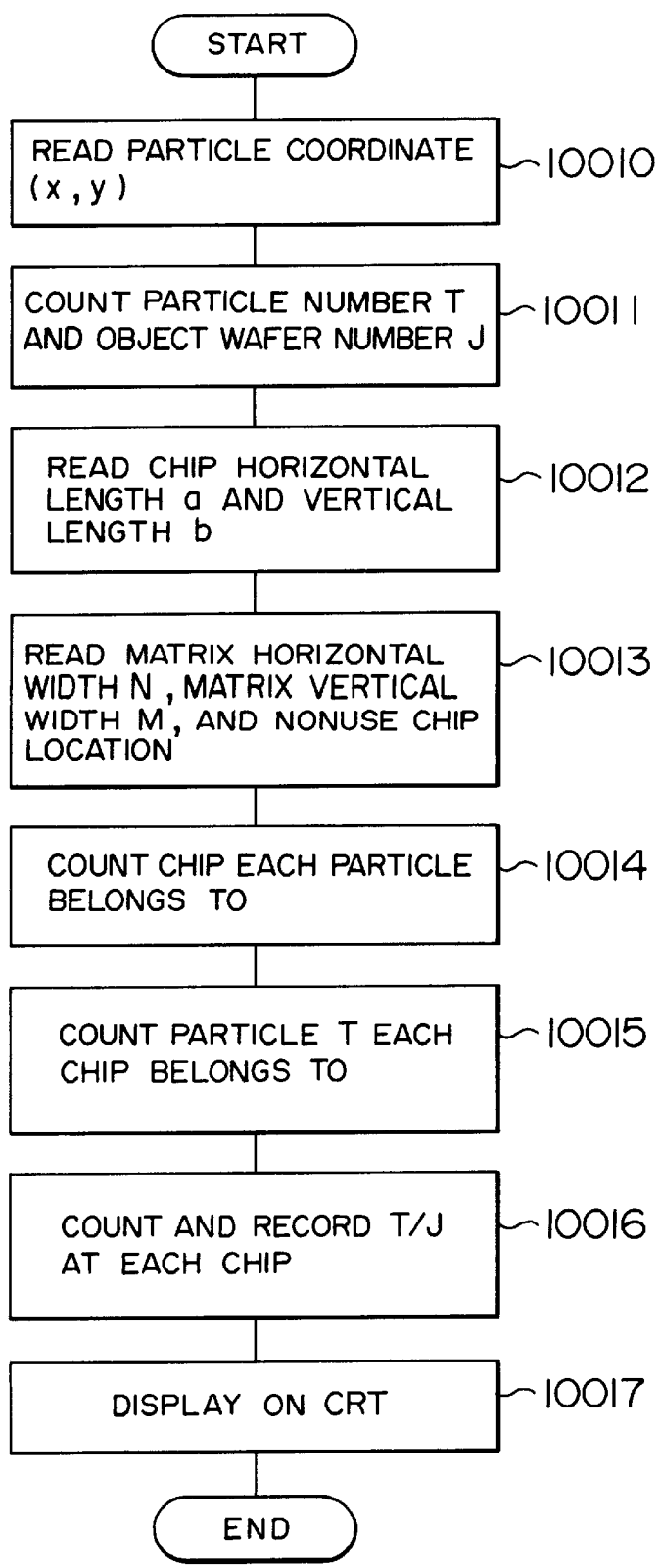
FIG. 22 is a flowchart showing an algorithm for determining which chip particles are attached.

Next, the description will be directed to an embodiment about the analysis with reference to FIGS. 21 and 22. This is referred to as a particle chip map. The particle data processing unit 1009 serves to perform a particle chip determining algorithm shown in FIG. 22 for counting the number of particles existing on each chip. An analysis operator has to specify a product name. And, he or she may specify a process name, a lot number, a wafer number, an inspection date, and an operation name if necessary. By the specification, the location coordiantes are retrieved from the particle database 1010 and are stored in the memory 1016 (step 10010). Then, the stored wafer number J is counted (step 10011). And, the chip horizontal width 1020, the chip vertical width 1019 (respectively denoted as a and b), the matrix horizontal width 1023, and the matrix vertical width 1022 are read into the particle data processing unit 1009 from the map information file saved in the internal harddisk 1017. The particle chip determining algorithm will be described later. In the present embodiment, the area of a (n, m)th chip will be represented as;

$(n-1)a < x < na$ $(m-1)b < y < mb$ where x and y respectively denote an X coordiante and a Y coordinate of each particle. The maximum value of (n, m) is (N, M). For each particle, n and m are calculated as follows (step 10014);

$n=[x/a]+1$ $m=[y/b]+1$

By the calculation, it is possible to find a chip to which the particles belong. Then, a two-dimensional exponent (n, m) is added to each particle. Herein, [z] represents a maximum integer which does not exceed a real number z. For each chip, the particle number is counted (step 10015) for deriving a particle density of each chip per wafer (step 10016). How particles exist on each chip is represented on the CRT 1013 by changing a chip color or meshing a chip according to each number of particles as shown in FIG. 21 (step 10017).

In addition, in FIG. 21, 1062 to 1065 represent the particle number sections per chip.

Embodiment 6

Next, the description will be directed to an embodiment of how to assist the analysis. This is referred to as the optional division of a wafer.

In the present embodiment, the particle data analysis station 2 serves to divide a wafer to be analyzed on the CRT 1013.

Figure 23:
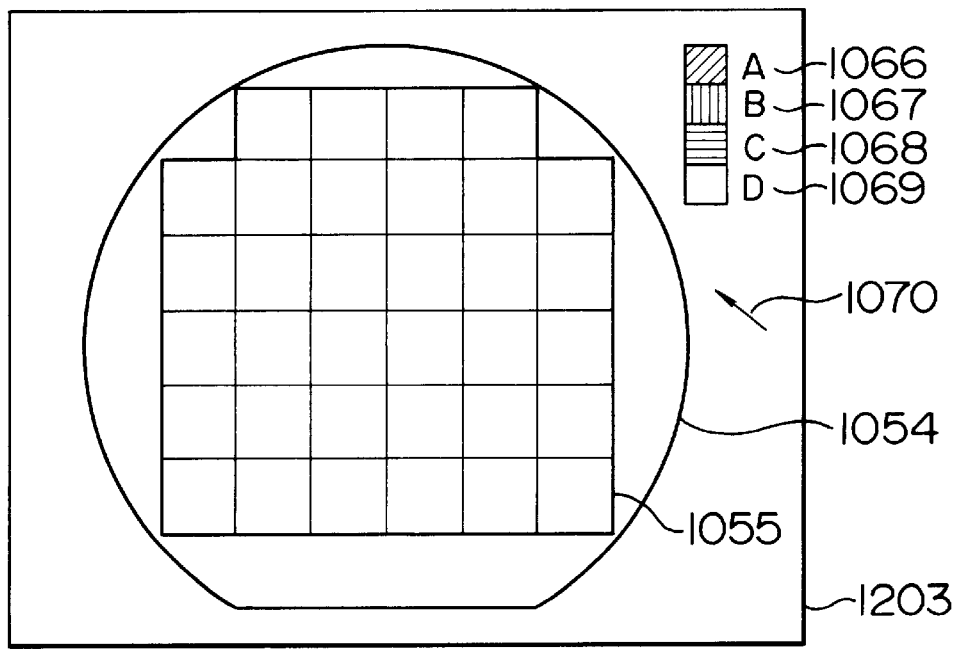
FIG. 23 is a view showing a screen output in case of optionally dividing a wafer.
Figure 24:
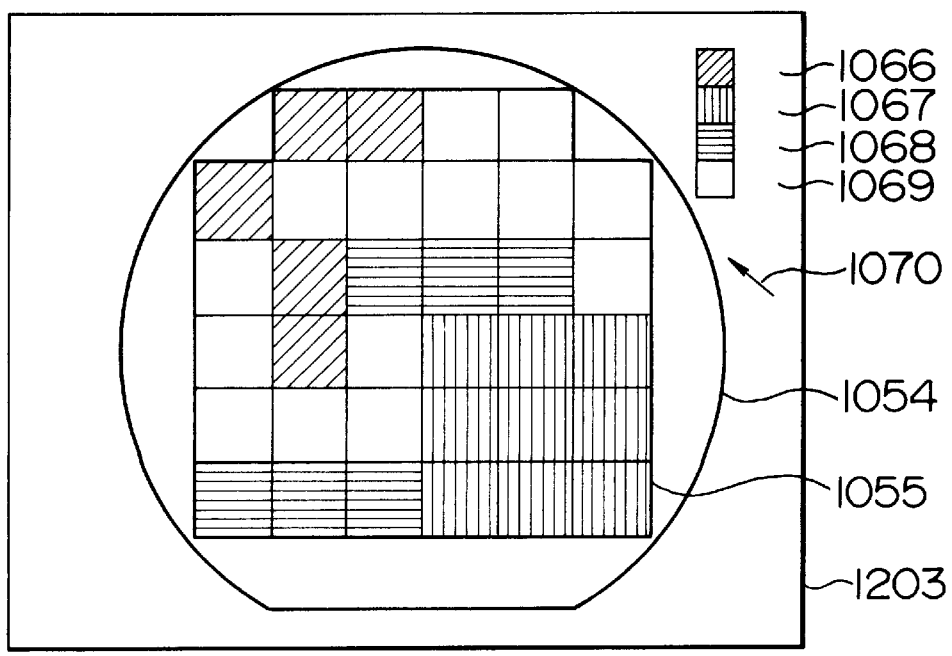
FIG. 24 is a view showing how a wafer is divided.

By specifying a product name, it is possible to display a wafer image on which the specified product chips are located on the CRT 1013 in a format shown in FIG. 23. And, an analysis operator specifies one of the area columns 1066 to 1069 on the screen by moving an arrow mark 1070 with the mouse 1012 and then specifies the chip by moving the arrow mark 1070 in order to separate the chips according to each particle density. Once one area of the area columns 1066 to 1069 is specified, the subsequently-specified chips are specified as the area. Each chip is divided by the color or the mesh according to each area. One example of the divided chips is shown in FIG. 24. The divided pattern is recorded as an optional divisional file shown in FIG. 25 in the harddisk 1017 included in the particle data analysis station 2. This recording is done according to each product.

Embodiment 7

Figures 25, 26:
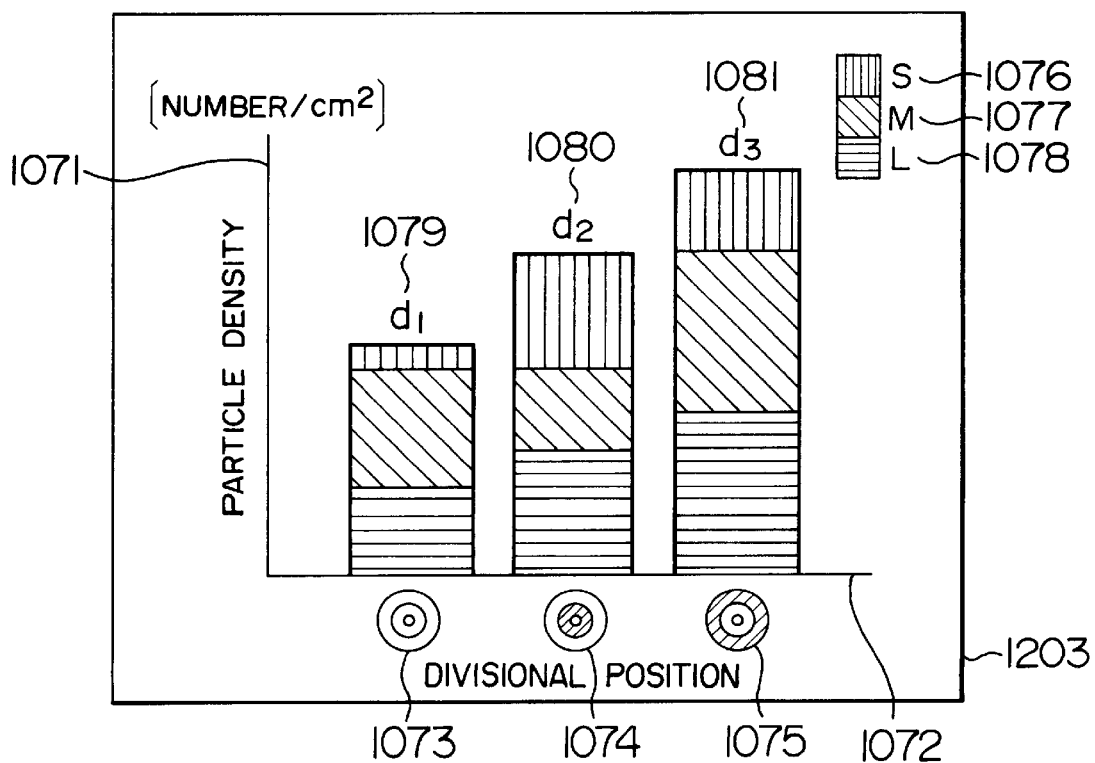
FIG. 25 is a chart showing a map information file.
FIG. 26 is a chart showing a particle density to divided locations of the wafer.

Next, the description will be directed to an embodiment about the analysis with reference to FIG. 26. The embodiment is referred to as wafer division.

The present embodiment is designed to divide a wafer into several areas and to calculate and output a particle density of each area.

Figure 27:
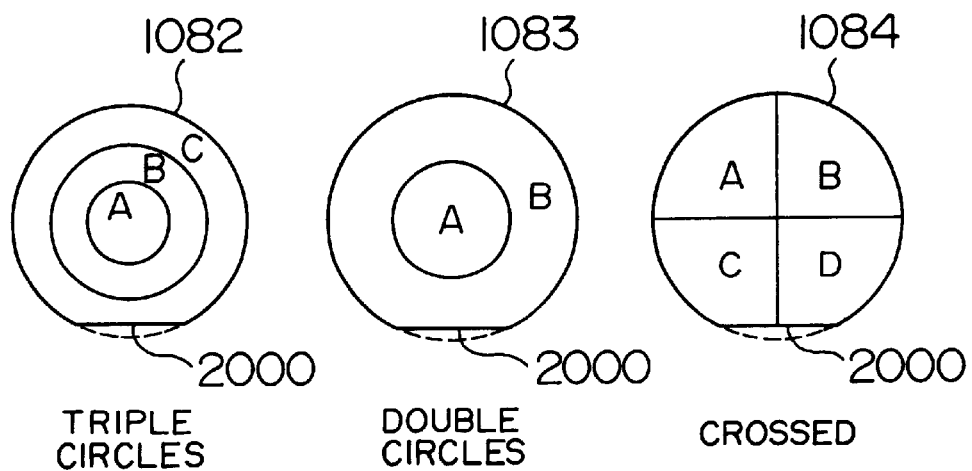
FIG. 27 is a view showing a pattern on which the wafer is divided.

In this embodiment, an analysis operator has to specify a product name and may specify a process name, a lot number, a wafer nubmer, an inspection date, and an operator name if necessary. By the specification, it is possible to save the particle location coordinates 5014, 5015 and the particle size 5016 as shown in FIG. 5C in the internal memory 1016 from the particle database 1010. And, the analysis operator specifies a divisional pattern of a wafer. The divisional pattern can be categorized as a formal divisional pattern such as a double circle 1083, a triple circle 1082, and a crossed pattern 1084 as shown in FIG. 27 and a pattern created by the wafer optional division specification described in the embodiment 5. The double circle and the triple circle are respectively created by equally dividing a radius of the wafer regarded as a circle into two or three. The crossed division is created by dividing the wafer by the perpendicular bisector of the orientation flat 2000 and a perpendicular passed through the center of the wafer.

The particle data processing unit 1009 derives a particle density of each area from the information about the particle location coordinates and the wafer area division and outputs the result in a graphical format. In the graph shown in FIG. 26, the axis of ordinate 1071 denotes a particle density (number/cm$^2$) and the axis of abscissa 1072 denotes three areas 1073, 1074, 1075 of the triple circle 1082. For obtaining quantitative data, it is possible to represent precise values ($d_1$) 1079, ($d_2$) 1080, and ($d_3$) 1081 at the top of each bar graph. The bar graph may be divided according to the particle sizes S 1076, M 1077, and L 1078 so that the divided sections may have respective colors or meshes. By specifying the mode change icon 1051, each divisional pattern for the analysis can be selected.

Embodiment 8

Figure 28:
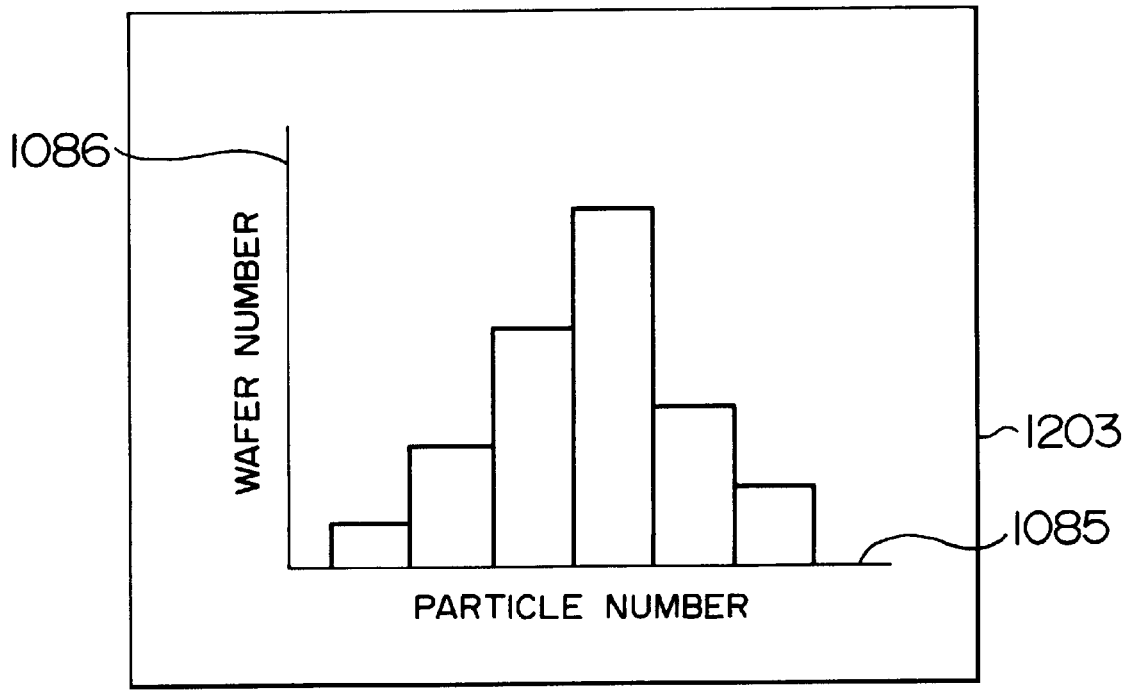
FIG. 28 is a chart showing how particles are distributed in a wafer.

Next, the description will be directed to an embodiment about the analysis with reference to FIG. 28. This embodiment is referred to as particle number frequency distribution.

The present embodiment is designed to represent the frequency distribution of the number of particles existing on one wafer.

An analysis operator has to specify a product name and a process name and may specify an inspection date, a lot number, and a wafer number if necessary. By the specification, it is possible to save the particle number 5010 shown in FIG. 5B in the external memory 1016 from the particle database 1010.

The particle data processing unit 1009 serves to derive the number of wafers for each range of the specified particle number and output on the screen the result as a histogram. In this graph, the axis of abscissa 1085 denotes the particle number, the maximum value and the divisional range which the analysis operator specifies. The axis of ordinance 1086 denotes the number of wafers.

Embodiment 9

Next, the description will be directed to an embodiment about the analysis. This embodiment is referred to as a particle trend chart.

The present embodiment is designed to output how the particle number is changed on time in the process specified by an analysis operator in a graphical manner.

The analysis operator has to specify a product name and a process name and may specify a wafer number, a lot number, an inspection date, and an operator name if necessary. By the specification, it is possible to save the inspection time 5006, the particle number 5010, and the particle size 5016 as shown in FIGS. 5A, 5B and 5C in the memory 1016 from the particle database 1010.

Figure 29:
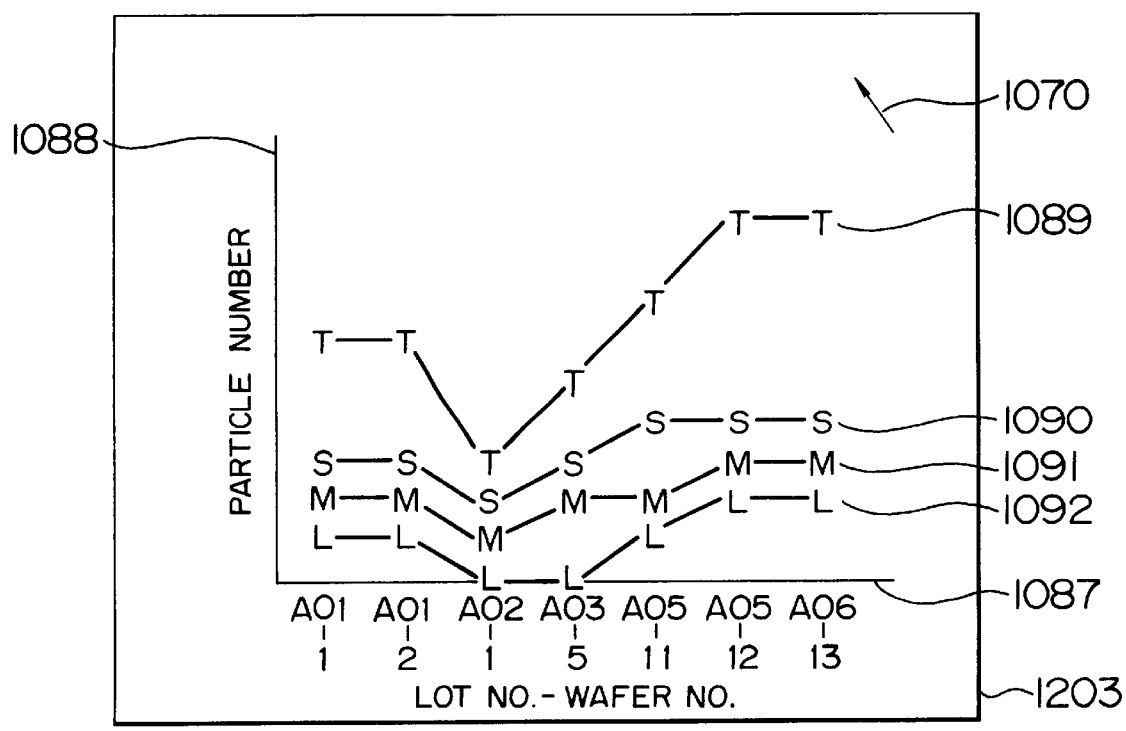
FIG. 29 is a chart showing a particle trend.
Figure 30:
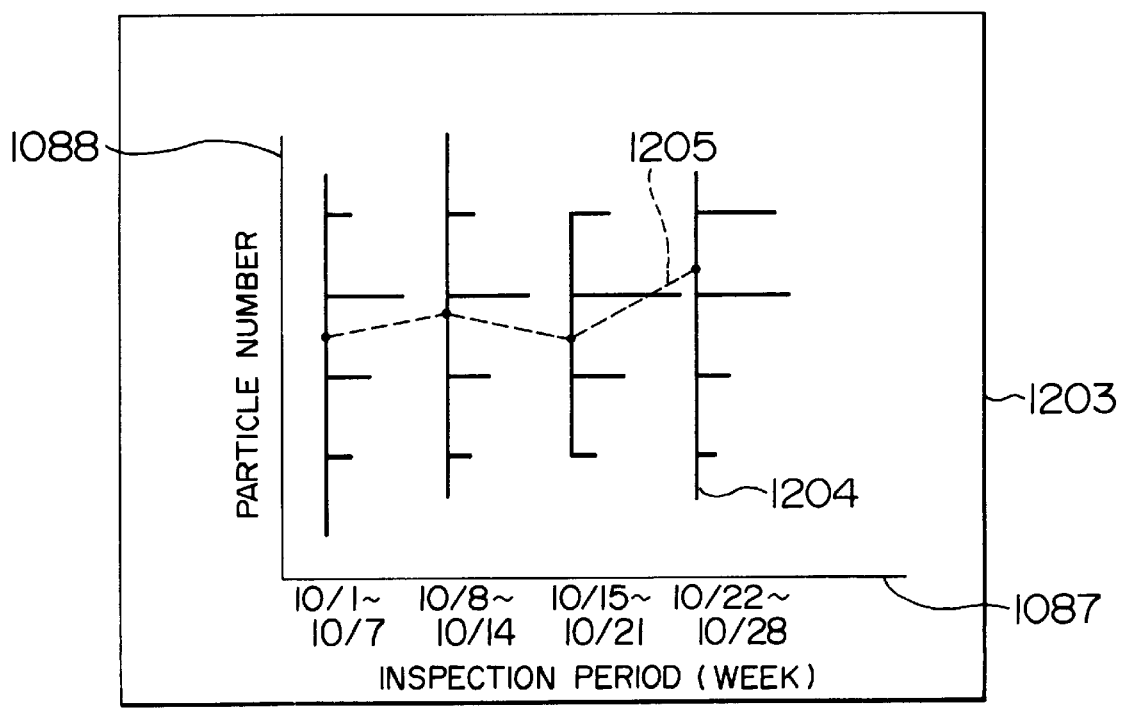
FIG. 30 is a chart showing frequency distributions of particle number in inspection periods and an average trend in each period.

The particle data processing unit 1009 serves to sort the information on time series and output the result in a graphical format. In the graph, the axis of abscissa 1087 denotes a time and the axis of ordinate denotes the particle number. As a unit for the axis of abscissa 1087, it is possible to employ any one of a wafer unit, a lot unit, a date unit, a week unit, and a month unit. In case of a wafer unit, as shown in FIG. 29, the particle data processing unit 1009 outputs a polygon for each of the particle sizes 1090 to 1092. In the polygon, 1089 denotes a total number. In case of a lot unit, a day unit, a week unit, and a month unit, it outputs particle frequency distribution 1204 for each unit in a graphical format shown in FIG. 30. In this graphical manner, it serves to calculate an average value 1205 for each unit and output the result on the frequency distribution 1204 in a polygon manner. The axis of abscissa is allowed to be horizontally scrolled by specifying a right or left half part of the graph with the mouse 1012 if it is impossible to display the information being processed on the screen. The axis of ordinate denotes a range to be selectively specified by the mode change icon 1051.

Embodiment 10

Figure 31:
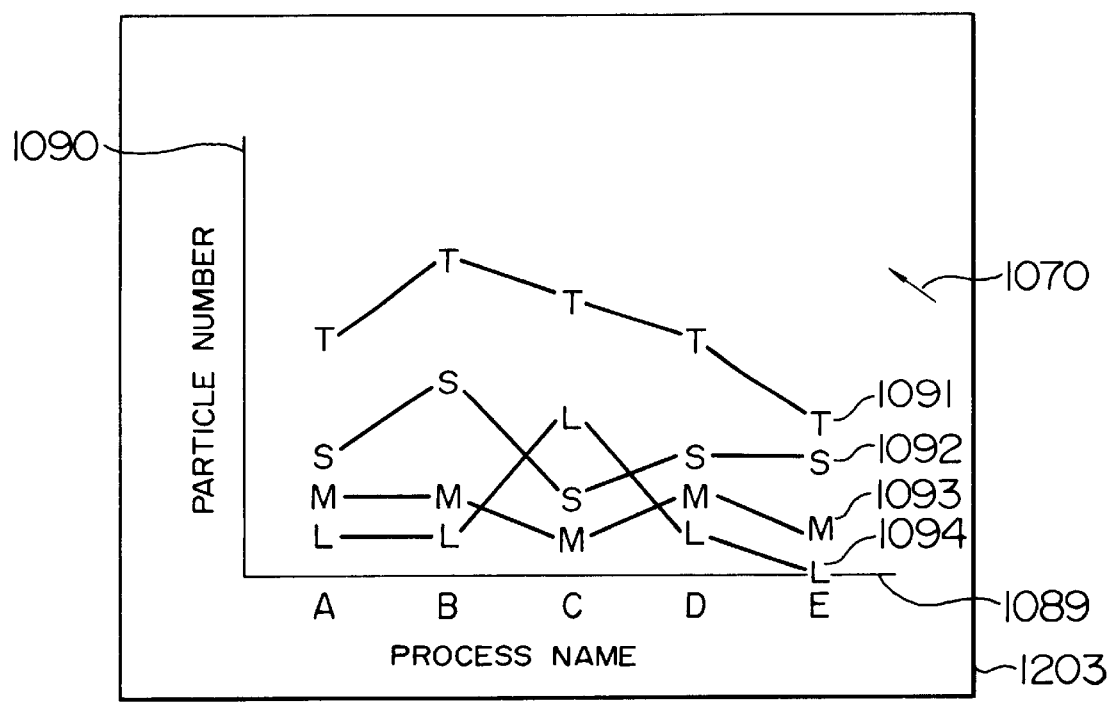
FIG. 31 is a chart showing how the particle number is changed in each sample process.

Next, the description will be directed to an embodiment of the invention with reference to FIG. 31. This embodiment is referred to as an inter-process particle trend.

The present embodiment is designed to output the particle trend on a wafer between processes in a polygon manner on the basis of the information measured in each process by the particle inspection machine 1.

By specifying more than one process name, it is possible to retrieve the information about the number of all particles 5010 for each wafer, the particle size 5016, and the inspection date and time 5005, 5006 from the particle database 1010 and save the retrieved information in the internal memory 1016.

The particle data processing unit 1009 serves to count the number of particles for each particle size, sort the process names in the inspection order given when the process name is specified, and output the particle number on the CRT 1013 as a polygon. In the polygon, it is possible to change lines and dots for each of the particle sizes (1092 to 1094) for displaying these size kinds of particles at the time of or separately from the number of all particles (1091). The axis of abscissa 1089 denotes the sequence of processes (inspection time series) and has fixed intervals. The axis of ordinate denotes an average particle number per wafer. If there exist so many specified processes that all of them are not displayed on the screen, it is possible to scroll the axis horizontally with the method described about the embodiment 9.

Embodiment 11

Figure 32:
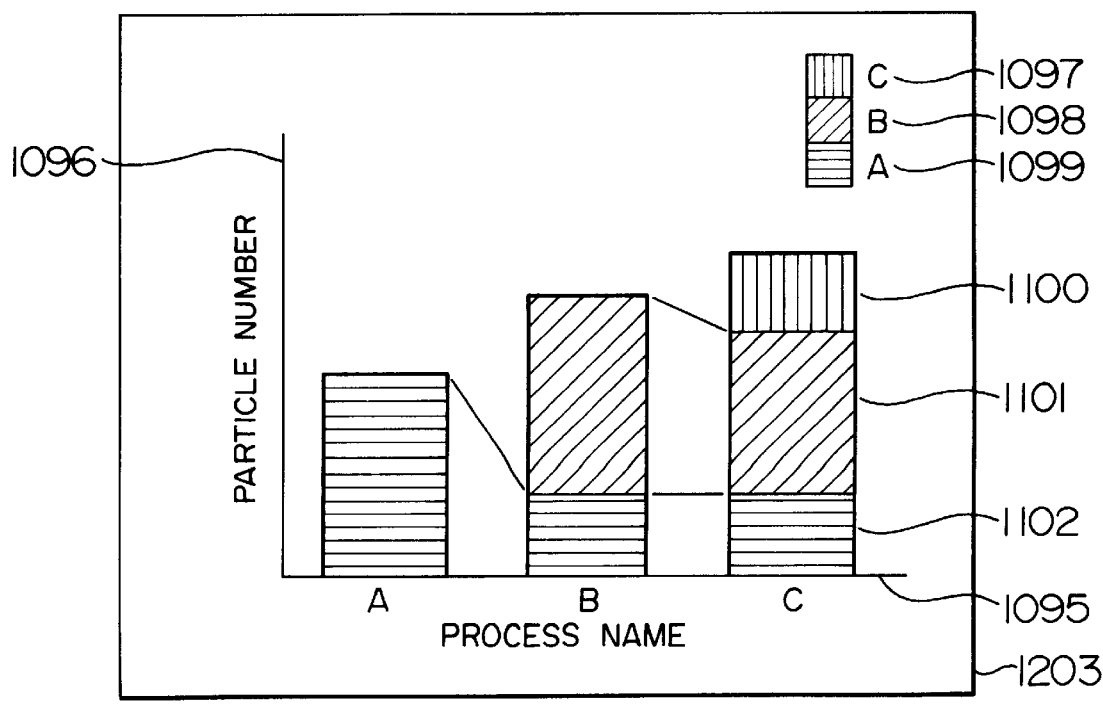
FIG. 32 is a chart showing the particle hysteresis.

Next, the description will be directed to an embodiment with reference to FIG. 32. This is referred to as particle hysteresis.

The present embodiment is designed to output how the particles are attached or removed in each process in a graphical manner.

An analysis operator has to specify a product name, more than one process name, and a lot number and may specify a wafer number if necessary. By the specification, it is possible to save the particle location coordinates 5014, 5015 on the specified wafer, the inspection date 5005, and the inspection time 5006 as shown in FIG. 5 in the memory 1016 from the particle database 1010.

Figures 33, 34:
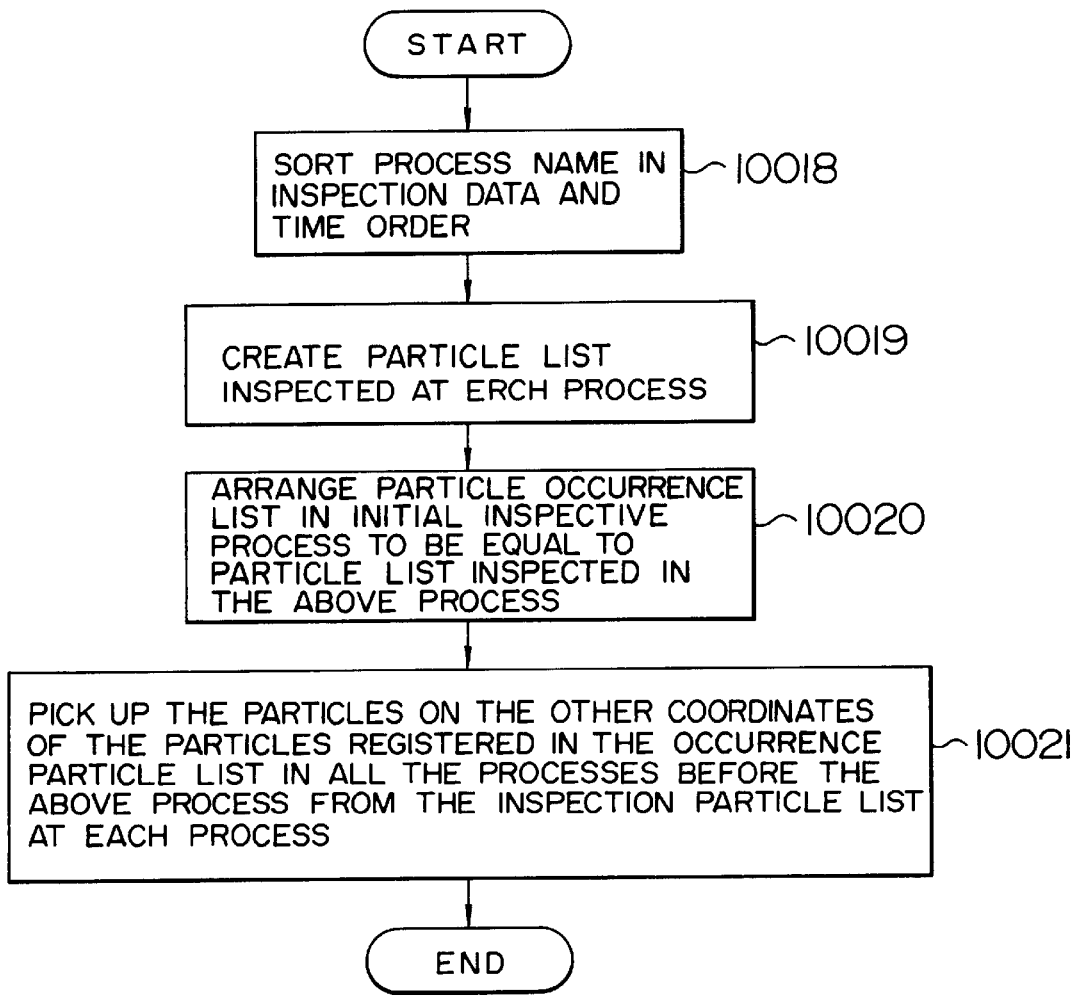
FIG. 33 is a flowchart showing an algorithm for particle trace.
FIG. 34 is a chart showing a format containing an inspected aprticle list and an existing particle list.

In the particle data processing unit 1009, the particle trace algorithm to be described later clearly indicates how the particles are attached or removed in each process. The particle trace algorithm will be described in FIG. 33. At first, the algorithm sorts the specified process names in earlier order by referencing the inspection date 5005 and the inspection time 5006 (step 10018). Then, it creates a sensed particle list for each process (step 10019) and then makes the caused particle list in the initial process identical to the sensed particle list therein (step 10020). The format of the sensed particle list is equal to that of the caused particle list, which is shown in FIG. 34. Next, the algorithm calculates a distance between the particle location coordinates on the wafer in the initial process and the particle location coordinates on the same wafer in the next process in the recording order of the coordinate data. If a calculated distance is smaller than a predetermined constant value R, these two particles about the distance are specified as the same. Then, the similar calculation is done about the next particle. If no particles in the second process are found to be equal to the particles sensed in the initial process, it is determined that the particles are removed. If no particles sensed in a process are found to be equal to the particles sensed in the previous process, it is determined that the particles are newly attached in the process. The particles to be newly attached in the new process are registered in the particle occurrence list in the new process (step 10021). The similar calculation is done in the order of the earlier processes.

As shown in FIG. 32, the particle data processing unit 1009 serves to output a bar chart in which the axis of ordinate 1096 denotes a particle number and the axis of abscissa 1095 denotes a process name. The process name is ranged from the left side in the earlier order. In the bar chart, the attached particles are separated in a layered manner in each process A, B or C (three layers 1100, 1101, 1102 shown in FIG. 32). These layers are respectively represented by colors and meshes and the line is drawn between the upper and the lower lines of one layer and those of another layer. If two or more wafers are specified, the process tracing is done for each wafer. What is displayed on the screen is an average value of these wafers.

Embodiment 12

Next, the description will be directed to an embodiment referred to as a process unit particle map.

The present embodiment is designed to extract only the particles attached on the wafer in the same process on the basis of the information measured by the particle inspection machine 1 in each process and then output the result as a particle map shown in FIG. 20.

An analysis operator has to specify a product name, two or more process names, and a lot number and may specify a wafer number if necessary. By the specification, the location coordinates 5014, 5015, the inspection date and time 5005, 5006, and the process name are saved in the internal memory 1016 from the database 1010.

The particle data processing unit 1009 serves to create the particle occurrence list in each process using the particle trace algorithm described about the embodiment 1. After finishing the procedure, the process unit particle map is displayed in the inspection process order. For displaying the next step, it is necessary to specify the mode change icon 1051.

Embodiment 13

Figure 35:
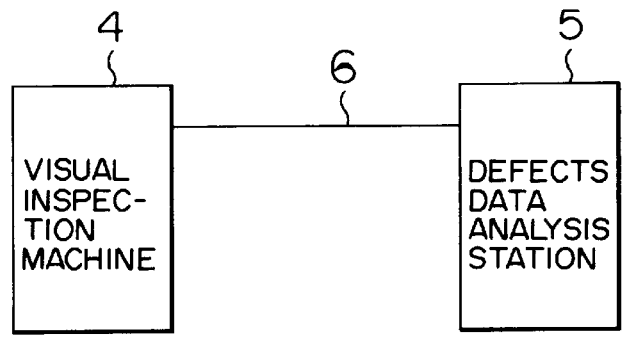
FIG. 35 is a view showing partial arrangement of the visual inspection system shown in FIG. 1.

With reference to FIG. 35, the present embodiment describes the visual inspection machine 4 and the defects data analysis station 5 in the inspection data analysis system mentioned about the foregoing embodiment 1. The present system comprises the visual inspection machine 4 and the defects data analysis station for analyzing the data supplied from the visual inspection machine 4. The visual inspection machine is connected to the defects data analysis station 5 through the communication line 6.

Figure 36:
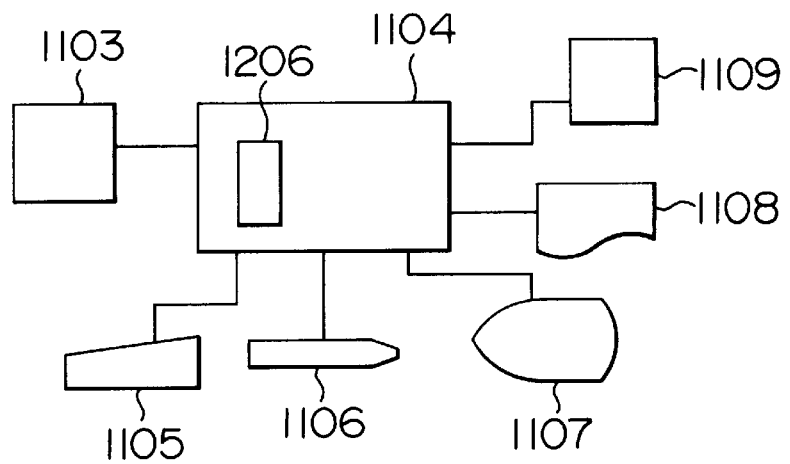
FIG. 36 is a view showing arrangement of the visual inspection machine shown in FIG. 35.

FIG. 36 illustrates the arrangement of the visual inspection machine 4, which comprises a defects sensing section 1103 for sensing particles and pattern defects generally referred to as defects, a defects sensing signal processing unit 1104, a memory 1206, a keyboard 1105, a bar-code reader 1106, both of which are served as an input unit, a CRT 1107, a printer 1108, both of which are served as an output unit, and an external communication section 1109 served to communicate with the defects data analysis station 5. The visual inspection machine 4 provides functions of recognizing two-dimensional coordinates, sizes, and kinds of the visual sensed defects on a wafer and counting the number of defects on the wafer, the number of critical defects, the number of critical defects in the inspected process, the number of defects chips, the number of critical defects chips, the number of cirtical defects chips in the process, and the number of inspection chips. The kind and cirtical level of the defects are determined by the analysis operator observing a defects image displayed on the CRT 1107. And, if the analysis operator determines that the observed defects are critical and caused in the inspected process, these defects are categorized as the critical defects in the inspected process. The number of defects chips, the number of critical defects chips, and the number of critical defects chips in the inspected process respectively means the number of chips including defects.

Figure 37:
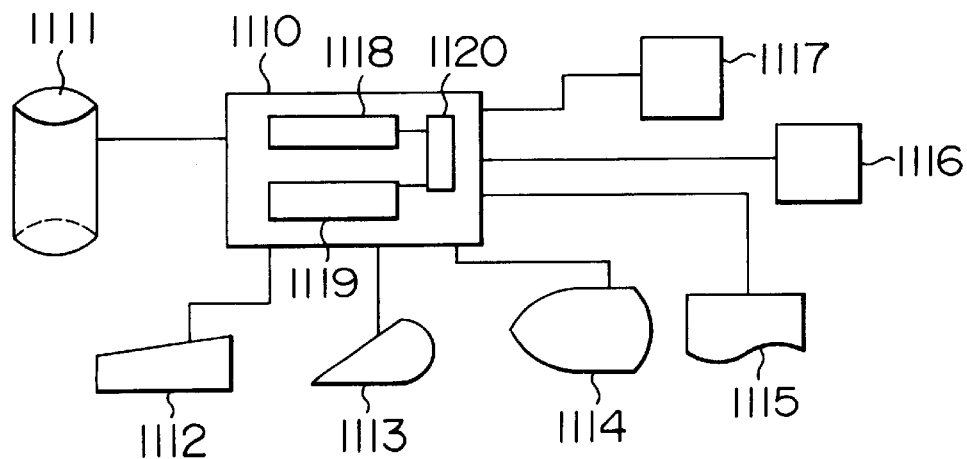
FIG. 37 is a view showing arrangement of the defects data analysis station shown in FIG. 35.

FIG. 37 illustrates the arrangement of the defects data analysis station 5, which comprises a defects data processing unit 1110, a defects database 1111, a keyboard 1112, a mouse 1113, both of which are served as an input unit, a CRT 1114, a printer 1115, both of which are served as an output unit, an external communication section 1116 serving to communicate with the visual inspection machine 4, a floppy disk drive 1117, a memory 1118 contained in the defects data processing unit, a harddisk 1119, and a CPU 1120.

The visual inspection machine 4 receives the defects management data such as a type of a wafer to be inspected, a process name to be inspected, a lot number, a wafer number, an inspection data and time, and an operator name, which are inputted by the keyboard 1105 or the bar-code reader 1106. The memory 1206 serves to save both of the defects inspection data and the defects management data. The defects inspection data contains the number of defects on an inspected wafer, the number of critical defects, the number of critical defects in the inspected process, the number of defects chips, the number of critical defects chips, the number of critical defects chips in the inspected process, the location coordinates of defects inside of the inspected chip, and the type and the critical level of the defects.

The arrangement of the defects database 1111 will be described with reference to FIG. 38. The basic arrangement is the same as that of the particle database 1010 described in the embodiment 2.

Figures 39, 40:
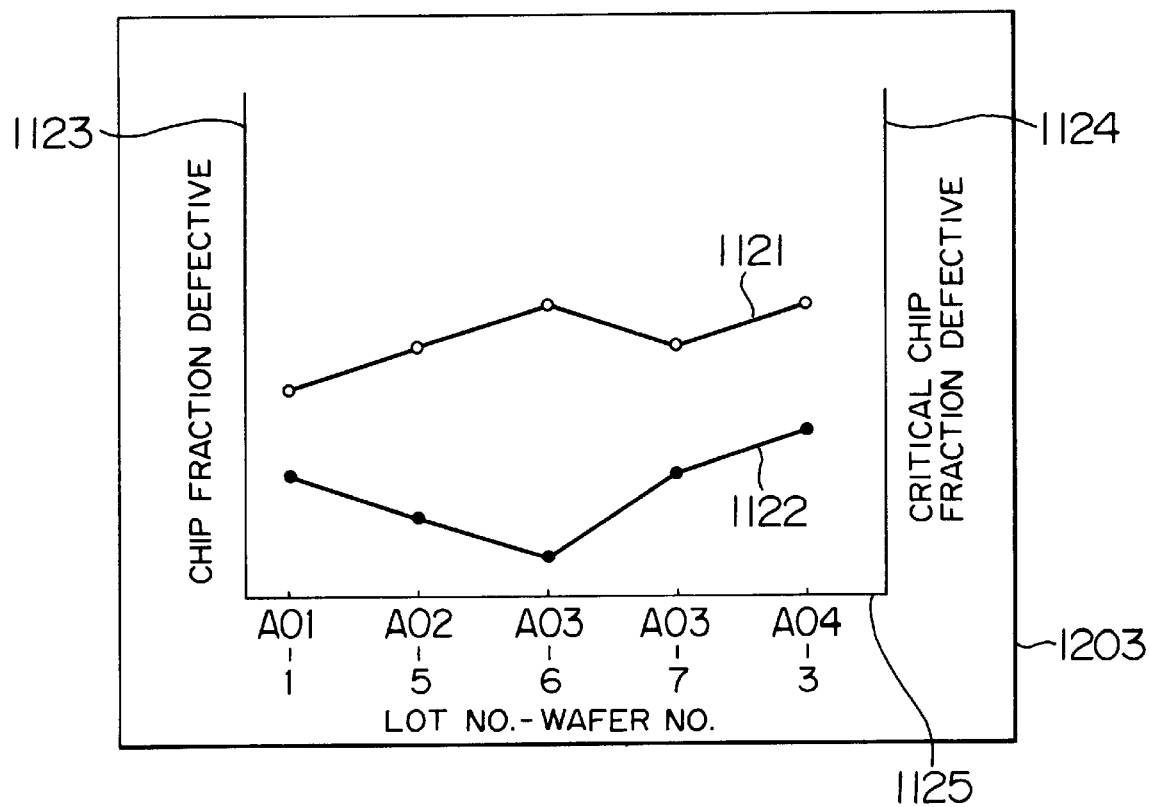
FIG. 39 is a chart showing a wafer number management file for each product.
FIG. 40 is a chart showing how a chip fraction defective is changed.
Figure 41:
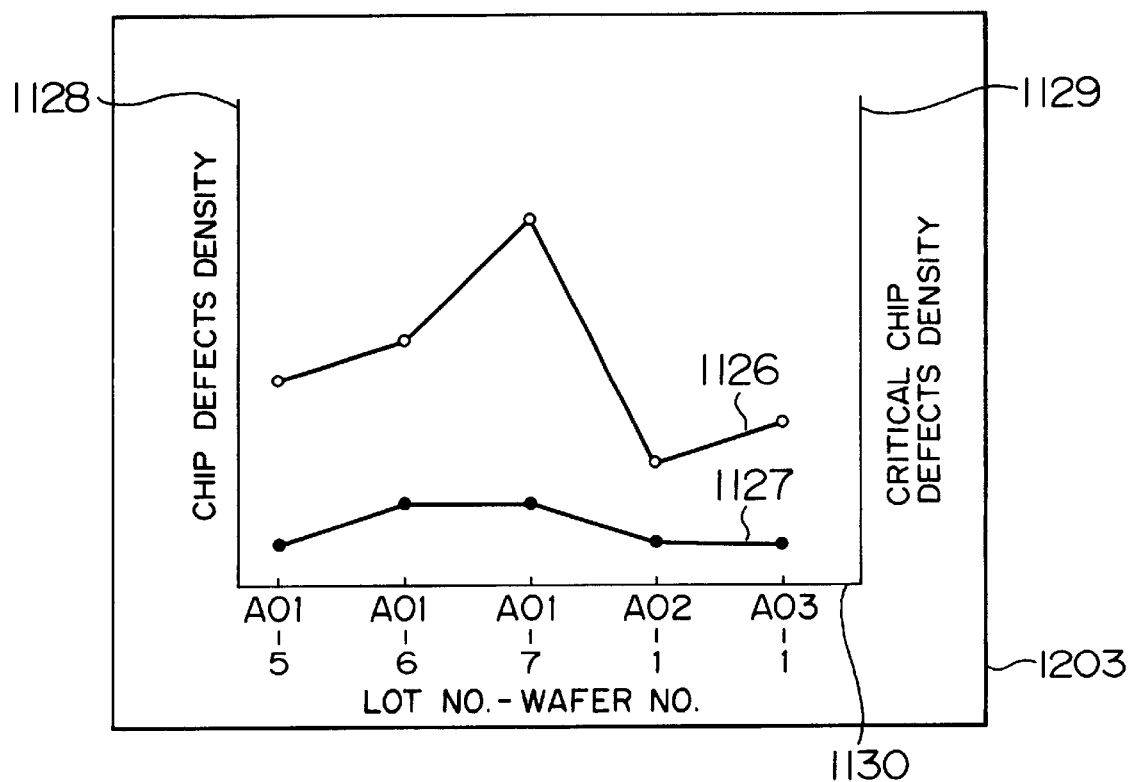
FIG. 41 is a chart showing how a chip defects density is changed.
Figure 42:
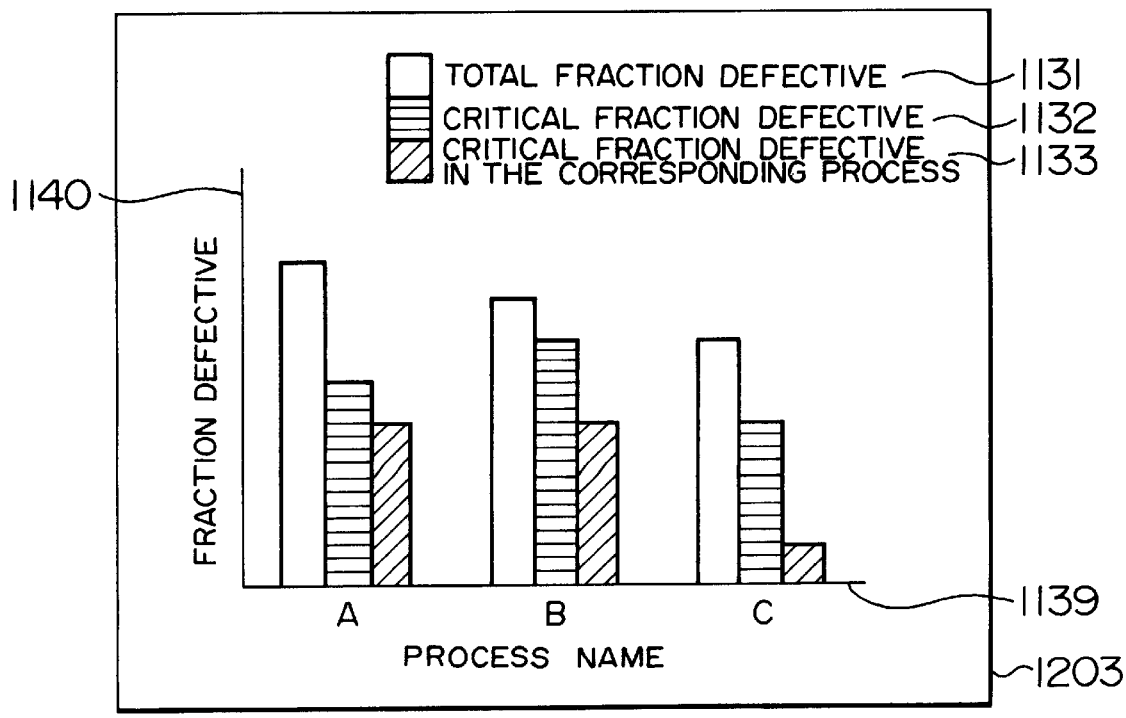
FIG. 42 is a chart showing a fraction defective in each sample process.

The particle defects data processing unit 1110 includes a product unit wafer number management file shown in FIG. 39, the map information file described in the embodiment 2, and the harddisk 1119.

Next, the flow of data will be described in the present system. After the visual inspection machine 4 finishes the inspection of one wafer, it sends the defects management data and the defects inspection data to the defects data analysis station 5 through the communication line 6. The subsequent flow is substantially same as the flow of data described in the embodiment 2, except that the processing data is the defects management data and the defects inspection data and is processed on a wafer unit.

Embodiment 14

This is an embodiment about how to use the defects data analysis station 5. It is generally same as the foregoing embodiment 3 about how to use the particle data analysis station 2. The different respect is that the basic data column 1036 displays the number of critical defects, a fraction defective, and a defect density in place of the number of l-sized particles, the number of M-sized particles, and the number of S-sized particles and the analysis function icon indicates analysis functions described in the embodiments 15 to 25.

Embodiment 15

Next, the description will be directed to an embodiment about the analysis. This embodiment is referred to as a defect map.

The present embodiment is generally same as the foregoing embodiment 4. The foregoing embodiment 4 has been designed to analyze particles using the particle inspection system described in the embodiments 2 and 3, while the present embodiment is designed to analyze defects using the visual inspection system described in the embodiments 13 and 14. In the output form, the embodiment 4 has represented the particle sizes by the colors or marks on the dots, while the present embodiment represents the categories of defects by the colors or marks.

Embodiment 16

Next, the description will be directed to an embodiment about the analysis. This embodiment is referred to as a defect chip map.

The present embodiment is generally same as the foregoing embodiment 5. The embodiment 5 has been designed to analyze particles using the particle inspection system described in the foregoing embodiments 2 and 3, while the present embodiment is designed to analyze defects using the visual inspection system described in the embodiments 13 and 14.

Embodiment 17

Next, the description will be directed to an embodiment about the analysis. This embodiment is referred to as wafer division.

The present embodiment is generally same as the foregoing embodiment 7. The embodiment 7 has been, designed to analyze particles using the particle inspection system described in the foregoing embodiments 2 and 3, while the present embodiment is designed to analyze the defects using the visual inspection system described in the embodiments 13 and 14.

Embodiment 18

Next, the description will be directed to an embodiment about the analysis. This embodiment is referred to as defect number frequency distribution.

The present embodiment is generally same as the foregoing embodiment 8. The embodiment 8 has been designed to analyze the particles using the particle inspection system described in the embodiments 2 and 3, while the present embodiment is designed to analyze the defects using the visual inspection system described in the embodiments 13 and 14.

Embodiment 19

Next, the description will be directed to an embodiment about the analysis. This embodiment is referred to as-defect trend.

The present embodiment is generally same as the foregoing embodiment 9. The embodiment 9 has been designed to analyze the particles using the particle inspection system described in the embodiments 2 and 3, while the present embodiment is designed to analyze the defects using the visual inspection system described in the embodiments 13 and 14. In the output form, the embodiment 9 has represented the particle sizes by the colors or marks on the polygonal lines and dots, while the present embodiment represents the categories of defects by them.

Embodiment 20

Next, the description will be directed to an embodiment about the analysis. This embodiment is referred to as inter-process defect trend.

The present embodiment is generally same as the foregoing embodiment 10. The embodiment 10 has been designed to analyze the particles using the particle inspection system described in the foregoing embodiments 2 and 3, while the present embodiment is designed to analyze the defects using the visual inspection system described in the embodiments 13 and 14. In the output format, the embodiment 9 has represented the particle sizes by the colors or marks on the polygon lines and the dots, while the present embodiment represents the categories of the defects by them.

Embodiment 21

Next, the description will be directed to an embodiment about the analysis. The embodiment is referred to as defect hysteresis.

The present embodiment is generally same as the foregoing embodiment 11. The embodiment 11 has been designed to analyze the particles using the particle inspection system described in the embodiments 2 and 3, while the present embodiment is designed to analyze the defects using the visual inspection system described in the embodiments 13 and 14.

Embodiment 22

Next, the description will be directed to an embodiment about the analysis with reference to FIG. 40. This embodiment is referred to as chip fraction defective trend. An analysis operator has to specify a product name, a process name, and an inspection date and may specify a lot number if necessary. By the specification, it is possible to save a lot number in the specified lot, a wafer number, a visual defect chip number 5045, a critical defect chip number 5044, an inspection chip number, an inspection time 5039 in the memory 1118 from the defects database 1111. The defect data processing unit serves to calculate the chip fraction defective and the critical chip fraction defective on the basis of the foregoing data in accordance with the following equations;

chip fraction defective=defects chip number/inspected chip number×100 critical chip fraction defective=critical defects chip number/inspected chip number×100

The data about each wafer is sorted in earlier order on the basis of the inspection date 5038 and the inspection time 5039.

On the CRT 1114 as an output form, the trends of the chip fraction defective 1112 and the critical chip fraction defective 1122 are displayed as polygons having respective colors or polygon types. In the polygon, the left-hand axis of ordinate 1124 denotes the chip fraction defective, the right-hand axis of ordinate 1125 denotes the critical chip fraction defective, and the axis of abscissa denotes the lot number and wafer number, which are displayed in the earlier order from the left hand.

Embodiment 23

Next, the description will be directed to an embodiment about the analysis. This embodiment will be referred to as chip defect density trend. An analysis operator has to specify a product name, a process name, and an inspection date and may specify a lot number if necessary. By the specification, it is possible to save a lot number and a wafer number in the inspected lot, a defects number 5043, an inspected chip number, and an inspection time 5039 in internal memory 1118 from the defects database 1111. The defects data processing unit 1110 serves to calculate a chip defects density and a critical chip defects density on the basis of the saved data in accordance with the following equations;

chip defects density=critical defects number/inspected chip number×100 critical chip defects density=critical defects number/inspected chip number×100

And, the data about each wafer is sorted in earlier order on the basis of the inspection date 5038 and the inspection time 5039.

On the CRT 1114 as an output form, the trends about the chip defects density and the critical chip defects density are displayed by polygons 1126 and 1127 having respective colors or polygon types. The left-hand axis of ordinate 1128 denotes a chip defects density, the right-hand axis of ordinate 1129 denotes a critical chip defects density, and the axis of abscissa denotes a lot number and a wafer number, which are displayed in earlier order from the left hand.

Embodiment 24

Next, the description will be directed to an embodiment about the analysis. This embodiment is referred to as a process unit fraction defective.

An analysis operator has to specify a product name and two or more process names and may specify a lot number, a wafer number, and an inspection date if necessary. By the specification, it is possible to save the corresponding lot and wafer numbers, a defective chip sum, a critical defective chip sum, a critical defective chip sum and an inspected chip number in the inspected process, an inspection date, and an inspection time in the internal memory 1118 from the defects database 1111. On the basis of the data, the defects data processing unit serves to calculate a total fraction defective 1131, a critical fraction defective 1132, and an inspected-process critical fraction defective 1133 in accordance with the following equations.

total fraction defective=defective chip sum/inspected chip sum×100 critical fraction defective=critical defective chip sum/inspected chip sum×100 inspected-process fraction defective=inspected-process critical defective chip sum/inspected chip sum×100 wherein if there exists data about two or more wafers in a process, the data is averaged about the wafers. The product names are sorted in earlier order on the basis of the inspection date 5038 and the inspection time 5039.

On the CRT 1114 as an output form, it is possible to display, in each process, the total fraction defective 1131, the critical fraction defective 1132, and the inspected-process critical fraction defective 1133 using polygons. In the polygons, the axis of abscissa 1139 denotes the processes, which are ranged in earlier order and the axis of ordinate 1140 denotes the fraction defectives having respective colors and meshes.

Embodiment 25

Figure 43:
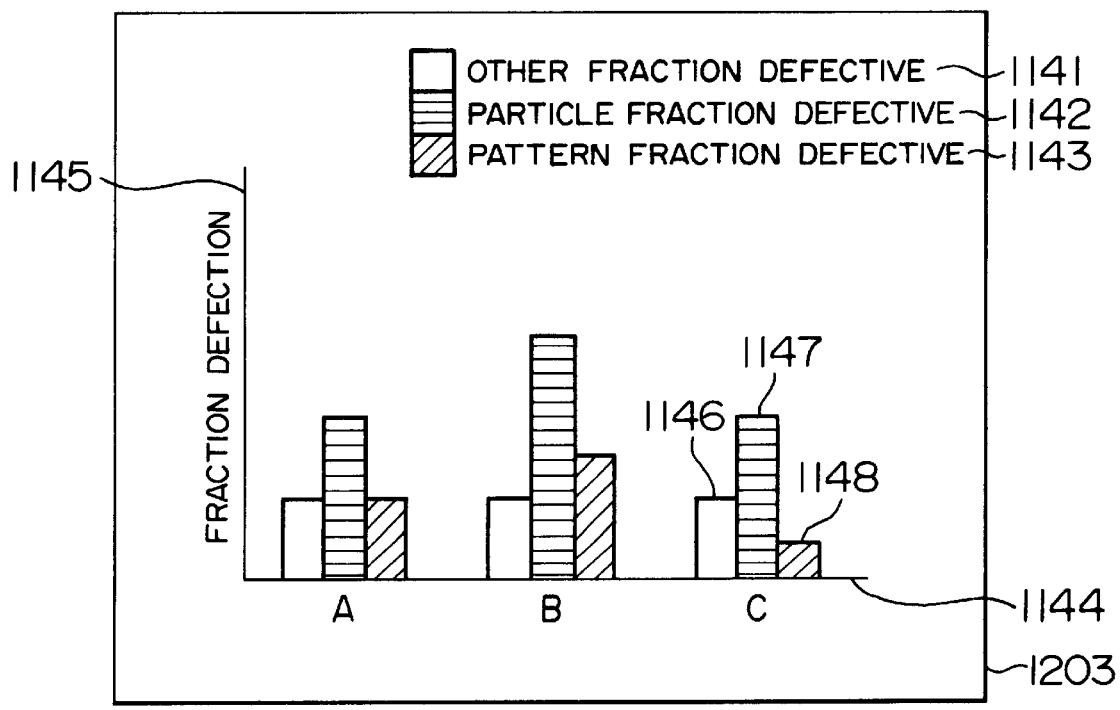
FIG. 43 is a chart showing another fraction defective in each sample process.

Next, the description will be directed to an embodiment about the other analysis method of a process unit fraction defective with reference to FIG. 43.

An analysis operator has to specify a product name and two or more process names and may specify a lot number, a wafer number, and an inspection date if necessary. By the specification, it is possible to save the corresponding lot and wafer numbers, a pattern-defect chip number, a particle-defect chip number, the other type defect chip number, an inspected chip number, an inspection date, and an inspection time in the internal memory 1118 from the defects database 1111. On the basis of the data, the defects data processing unit serves to calculate a fraction defective of the pattern-defect chip, a fraction defective of the particle-defect chip, and a fraction defective of the other type-defect chip in accordance with the following equations;

fraction defective of the pattern-defect chip=pattern-defect chip number/inspected chip number×100 fraction defective of the particle-defect chip=particle-defect chip number/inspected chip number×100 fraction defective of the other type-defect chip=the other type-defect chip number/inspected chip number×100 wherein if there exists data about two or more wafers in a process, the data is averaged about the wafers. The process names are ranged in earlier order on the basis of the inspection date and the inspection time.

On the CRT 1114 as an output form, it is possible to display, for each process, the pattern-defect chip fraction defective 1143, the particle-defect chip fraction defective 1142, and the other type-defect chip fraction defective 1141 using polygons 1148, 1147, 1146. In the polygons, the axis of abscissa 1143 denotes the processes, which are ranged in earlier order from the left hand and the axis of ordinate denotes the fractions defective having respective colors or meshes.

Embodiment 26

The present embodiment is designed to have the particle inspection machine 1, the particle data analysis station 2, the probing tester 7, and the probing test data analysis station 8 as included in the inspection data analysis system described in the foregoing embodiment 1. The present embodiment will be illustrated in FIG. 44.

Figure 45:
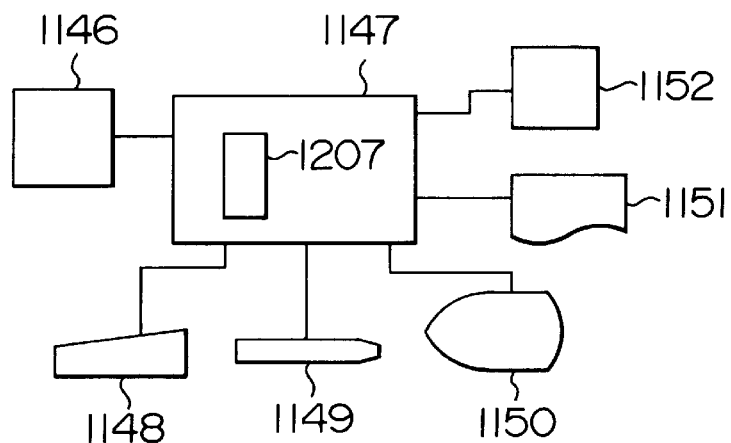
FIG. 45 is a diagram showing arrangement of the probing tester.

FIG. 45 illustrates the arrangement of the probing tester 7, which comprises a probing test unit 1146, a probing data inspection and processing unit 1147, a keyboard 1148, a bar-code reader 1149, both of which are served as an input unit, a CRT 1150, a printer 1151, both of which are served as an output unit, an external communication unit 1152 for communicating with the probing test data analysis station 8, and a memory 1207 contained in the data processing unit 1147. This probing tester 7 serves to test a product character of semiconductor devices integrated on a wafer.

Figure 44:
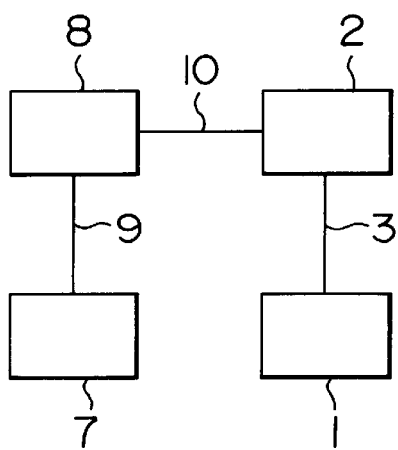
FIG. 44 is a diagram showing a particle inspection machine, a particle data analysis station, a probing tester, and a probing test data analysis station, which correspond to partial arrangement of the system shown in FIG. 1.
Figure 46:
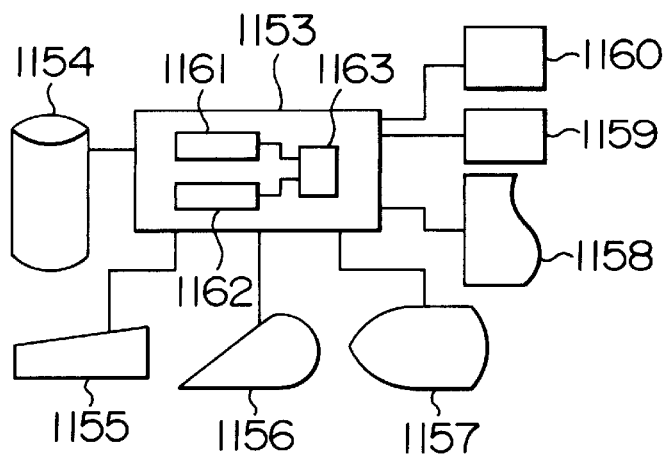
FIG. 46 is a diagram showing arrnagement of the probing data analysis station.

FIG. 46 illustrates the arrangement of the probing test data analysis station 8, which comprises a probing data processing unit 1153, a probing database 1154 for saving the result supplied by the probing data processing unit 1153, a keyboard 1155, a mouse 1156, both of which are served as an input unit, a CRT 1157, a printer 1158, both of which are served as an output unit, a first external communication unit 1159 for communicating with the probing tester 7, a second external communication unit 1160 for communicating with the particle data analysis station 2, a memory 1161, a harddisk 1162, and a CPU 1163. The arrangement of the particle data analysis station 2 shown in FIG. 44 is generally same as that described in the embodiment 2 and shown in FIG. 4, except that it additionally provides an external communication unit 1164 for communicating with the probing data inspection analysis station 8 (see FIG. 47).

Figure 6:
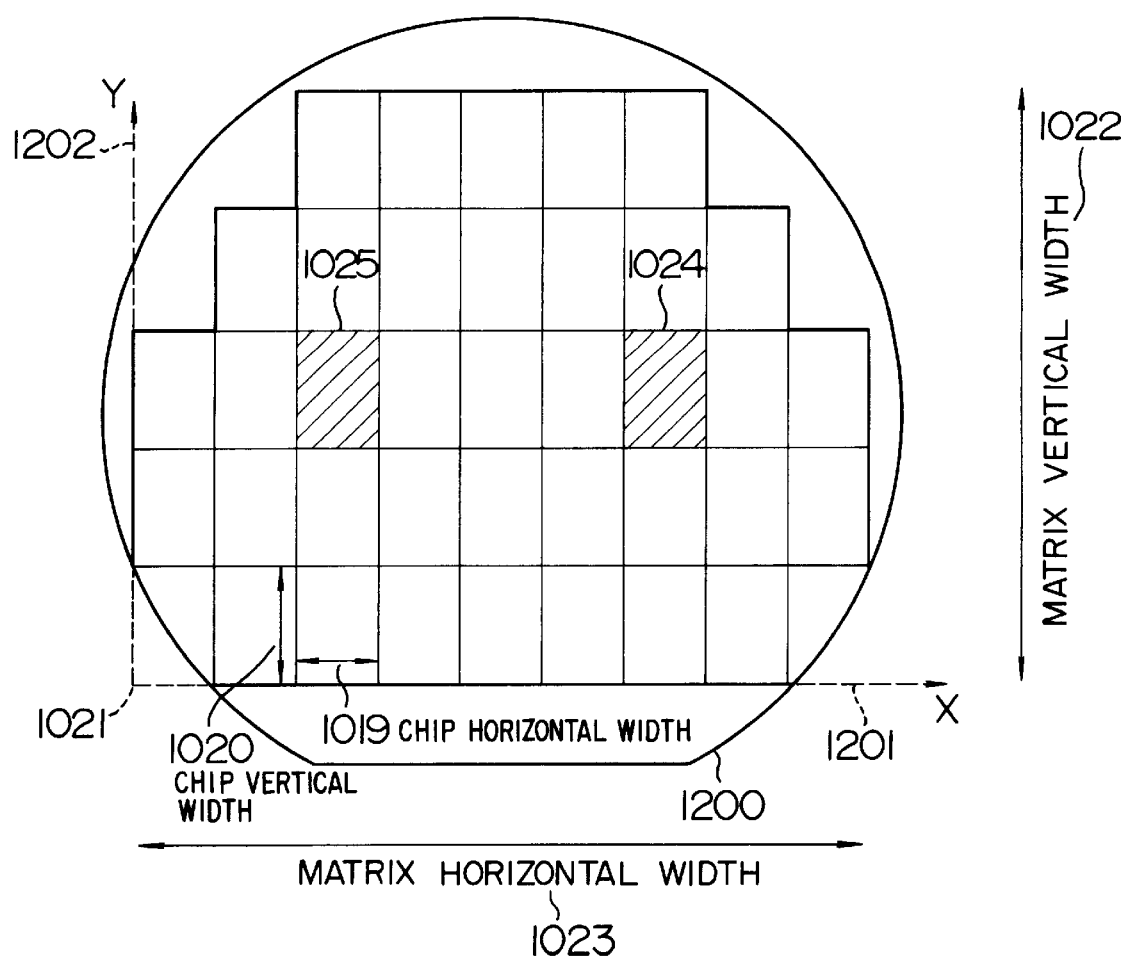
FIG. 6 is a view showing how to set a particle coordinate system.

When the wafer is inspected, the probing tester 7 receives probing management data input by the keyboard 1148 or the bar-code reader 1149. The probing management data contains a type of the inspected wafer, a lot number, a wafer number, an inspection date and time, and an operator name. The probing tester 7 serves to test an electric characteristic of a chip on the inspected wafer and save the probing test data consisting of the inspected result and the location of the chip together with the probing management data. The coordinate system described in the embodiment 2 and shown in FIG. 6 is used for showing the location of the chip. When the probing tester 7 finishes the inspection of one slot, the probing test data analysis station 8 reads the probing management data and the probing test data of the inspected lot from the probing tester 7. Then, it serves to determine if the product is defective on the basis of the probing test data and register the result in the probing database 1154 as shown in FIG. 48. The probing database 1154 includes two data tables, that is, a probing test lot data table (see FIG. 48A) for the probing management data 1146 to 1150 except the wafer number and a probing test wafer data table (see FIG. 48B) for the lot number 1151, the wafer number 1150, and the probing test data 1153 to 1156.

The arrangement of the particle database 1010 is same as that described in the embodiment 2.

The particle data processing unit 1009 includes an analysis data auxiliary file shown in FIG. 49, a map information file described in the embodiment 2, and a product unit lot number management file. The analysis data auxiliary file contains the estimated product number 1158 per wafer registered in each product. The function of the product unit lot number management file is generally same as that described in the embodiment 2, except that when the product unit lot number becomes zero, the data about the product is deleted from the analysis auxiliary file.

Embodiment 27

The present embodiment concerns with how to use the particle data analysis station 2 described in the embodiment 26. The way of use is generally same as that of the particle data analysis station 2 described in the embodiment 3, except that the analysis function icons additionally have analysis functions described in the embodiments 28 to 31.

Embodiment 28

Figure 50:
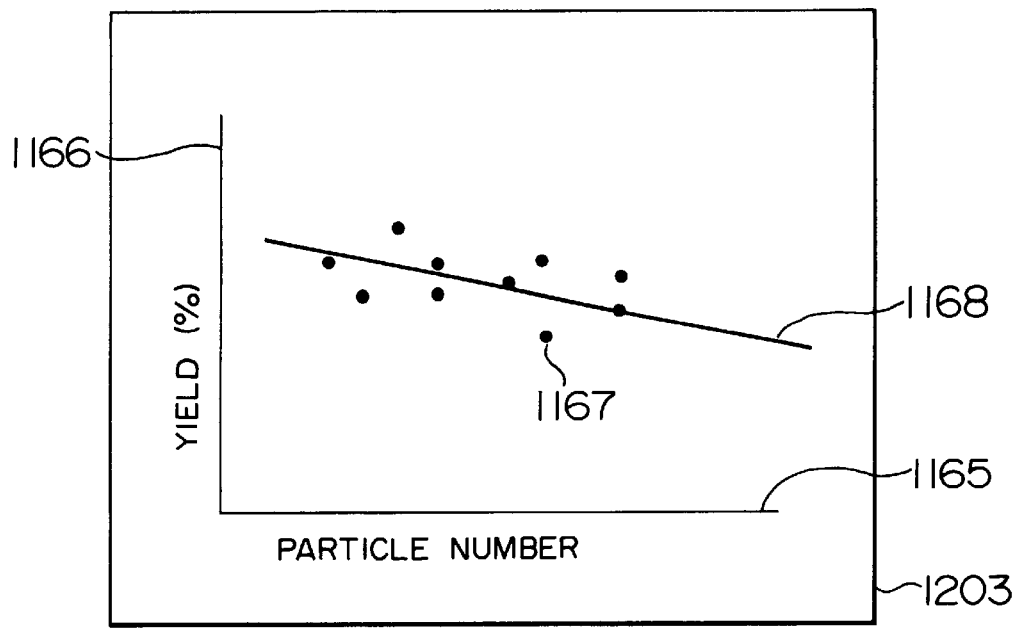
FIG. 50 is a chart showing correlation analysis between a particle number and a yield.

Next, the description will be directed to an;, embodiment referred to as correlation analysis about, a particle yield with reference to FIG. 50.

Figure 51:
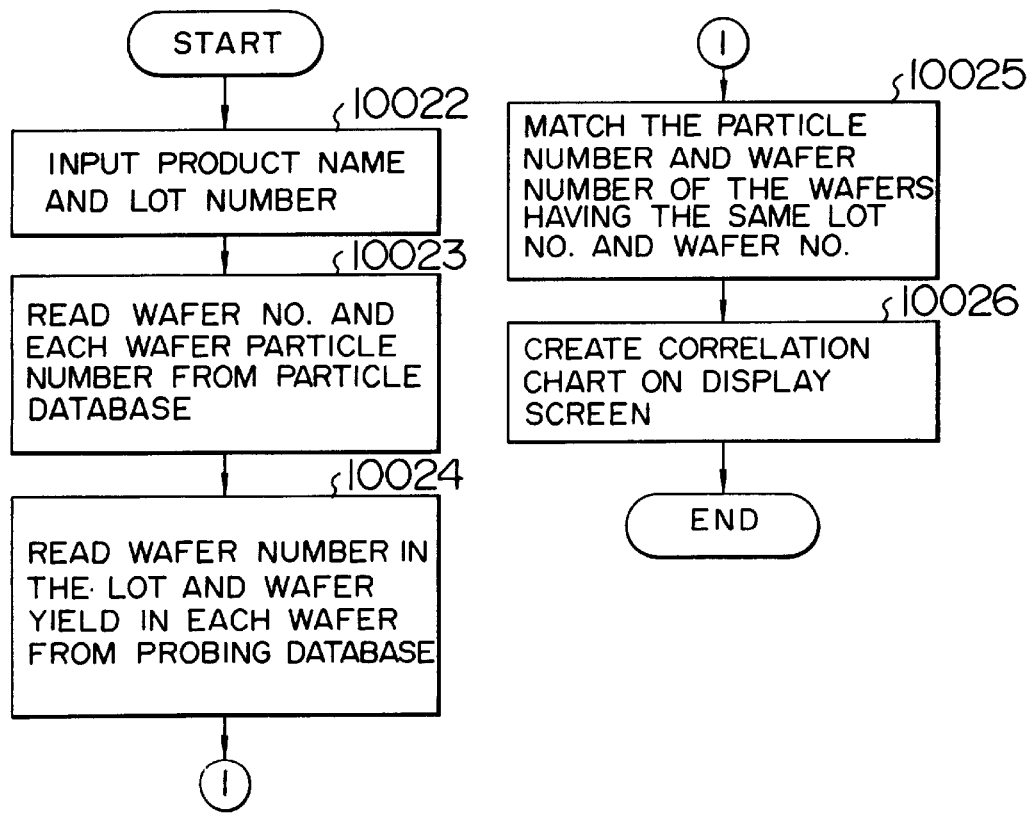
FIG. 51 is a flowchart for deriving correlation between the particle number and the yield.

The present embodiment serves to output as a correlation chart the relation between the particle number existing on a wafer being processed and a probing test yield given after the wafer processing process is over. The algorithm for the data analysis is illustrated in FIG. 51.

An analysis operator specifies a product name and a lot number (step 10022). By the specification, it is possible to save the wafer number of the specified lot and the particle number of each wafer in the internal memory 1118 from the particle database 1010 (step 10023) and yields of wafers in the specified lot in the memory 1118 from the probing data test station 8 (step 1024). The particle data processing unit 1009 serves to match the particle number to the wafer yield according to the wafer number (step 10025) and create the correlation chart (step 10026). As an output format, the axis of abscissa 1165 denotes the particle number and the axis or ordinate 1166 denotes the yield represented by a percent unit. Several dots 1167 are provided for calculating a primary regression line 1168 and depicting it on the chart.

Embodiment 29

Next, the description will be directed to an embodiment about the analysis with reference to FIG. 52. This embodiment is referred to as particle yield overlay trend.

The present embodiment is designed to output as polygons a trend about the number of particle existing on a wafer being manufactured and a trend about a probing test yield of the manufactured wafer.

An analysis operator has to specify a product name and an inspection period and may specify a lot umber if necessary. By the specification, it is possible to save an inspection date 5005, an inspection time 5006, a wafer number 5009, and a particle number 5010 of the lot matching to a retrieval condition shown in FIG. 5 in the internal memory 1118 from the particle database 1010 and the probing data of the wafer in the internal memory 1118 from the probing test data analysis station 8. The particle data processing unit 1009 serves to sort the wafers in earlier order on the basis of the inspection date and time. As an output format, the axis of abscissa 1175 denotes the wafer numbers, which are ranged from the left. The right-hand axis of ordinate 1169 denotes a particle number and the left-hand axis of ordinate 1170 denotes a wafer yield. The dots 1171 indicating the number of particles existing on the same wafer and the dots 1172 indicating yields are given on the same vertical axis so that both of those dots are connected for creating two polygons 1173, 1174. Two polygons have respective colors or kinds of polygons.

Embodiment 30

Figure 53:
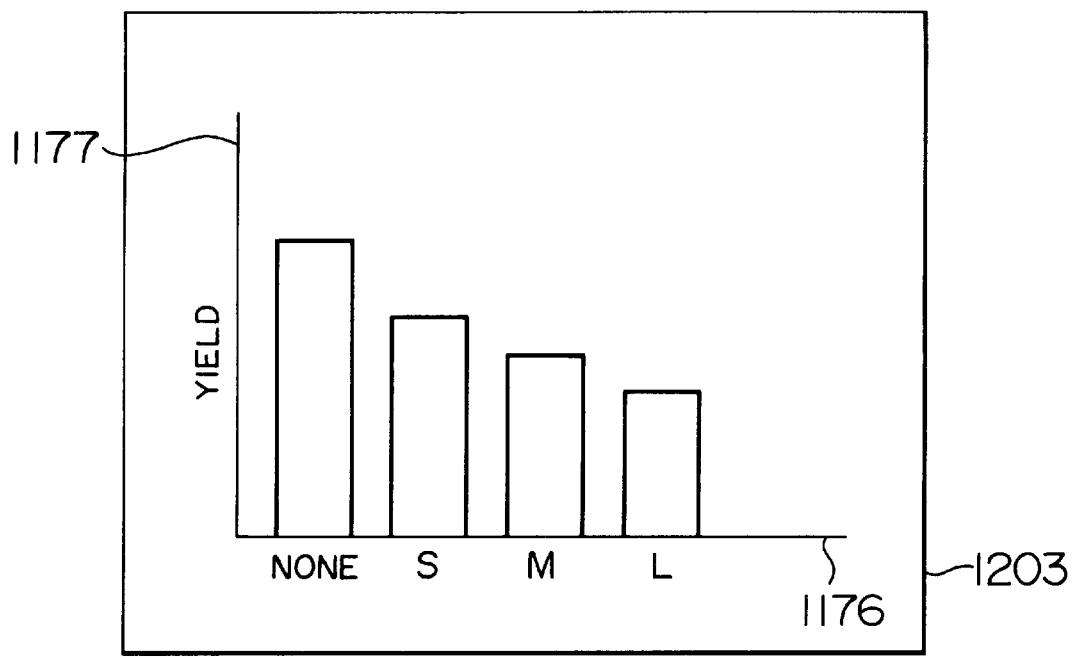
FIG. 53 is a chart showing a yield for each particle diameter size.

Next, the description will be directed to an embodiment about the analysis with reference to FIG. 53. This embodiment is referred to as a yield for each particle size.

The present embodiment is designed to output as a bar-chart the relation between a particle size on a wafer being manufactured and a probing test yield of the manufactured wafer.

An analysis operator has to specify a product name, a process name, and a lot number. By the specification, it is possible to save a wafer number in the specified lot, particle location coordiantes 5014, 5015 on each wafer, and a particle size 5016 in the internal memory from the particle database 1010 and a wafer number in the specified lot and a determined result, good or defective, of each chip existing on the wafer from the probing test data station 8. The particle size is categorized into three classes of L, M, and S in larger order as described in the foregoing embodiment 1.

The particle data processing unit 1009 serves to determine the particle chips existing on each wafer and record their particle sizes on the basis of the chip arrangement information and the particle location coordinates. For doing so, the particle data processing unit 1009 employs the particle chip determining algorithm as described in the embodiment 5. For recording the particle size, if two or more particles exist on one chip, the largest particle size is representatively used. The chips are categorized into four classes of L-, M-, and S-sized particle chips and no particle chips. For each class, a yield is derived. In the present embodiment, the yield is defined for each particle size by the following equation:

yield for particle size=the number of goods in a particle chip for each particle size/the number of particle chips for each particle size×100

On the CRT 1013 as an output form, the axis of abscissa 1176 denotes the particle sizes, which are ranged from no particles, S-sized particles, M-sized particles, and L-sized particles from the left. The axis of ordinate 1177 denotes a yield for each particle size, which is displayed on each particle size denoted by the axis of abscissa of the bar chart.

Embodiment 31

Figure 54:
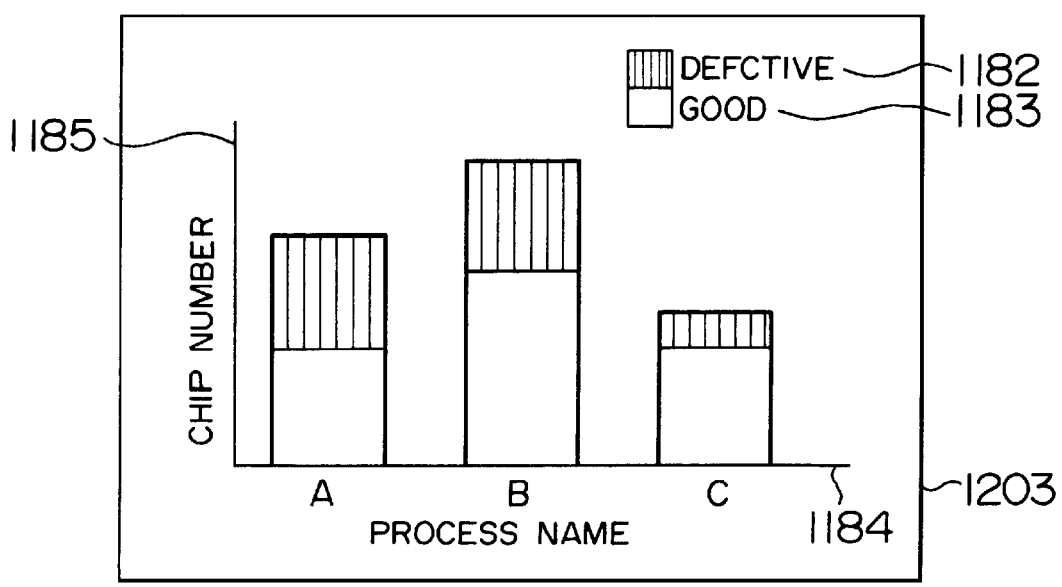
FIG. 54 is a chart showing a fraction defective in each sample processes.

Next, the description will be directed to an embodiment about the analysis with reference to FIG. 54. This embodiment is referred to as a fraction defective in each process in which particles are attached on a wafer (referred to as a particle process). The present embodiment is designed to output a probing test yield of the manufactured wafer in each particle process as a bar chart form.

An analysis operator has to specify a product name, two or more process names, and a lot number. By the specification, it is possible to save the inspection date 5005 and the inspection time 5006 as shown in FIG. 5, a wafer number 5013 of the lot, and particle location coordinates 5014, 5015 on each wafer in the internal memory from the particle database 1010 and the wafer number of the lot and the determined result, good or defective, of each chip in the wafer in the internal memory from the probing test data analysis station 8.

The particle data processing unit 1009 serves to create a particle extracting map for each process as described in the foregoing embodiment 12. For the particle extracting map for each process, the particle-attached chip determining algorithm is used for determining if the particles are attached on each chip. The unit 1009 serves to count the number of the particle-attached chips for each process and the number of goods existing in the particle-attached chip. The output is displayed in the CRT 1013, in which the axis of abscissa 1184 denotes the process names ranged in earlier order from the left and the axis of ordinate 1185 denotes the chip number. For each process A, B, or C, the bar chart indicating the number of the particle-attached chips is created. The bar chart is categorized into two layers in which the lower layer denotes the number of goods 1183 contained in the particle-attached chip and the upper layer denotes the number of defectives 1182 contained therein. These layers have respective colors and meshes.

Embodiment 32

Figure 55:
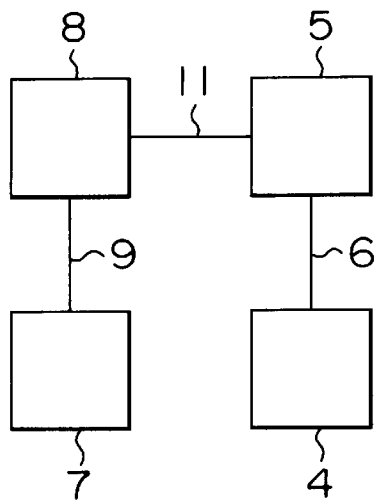
FIG. 55 is a diagram showing a visual inspection machine, which is part of the system shown in FIG. 1.
Figure 56:
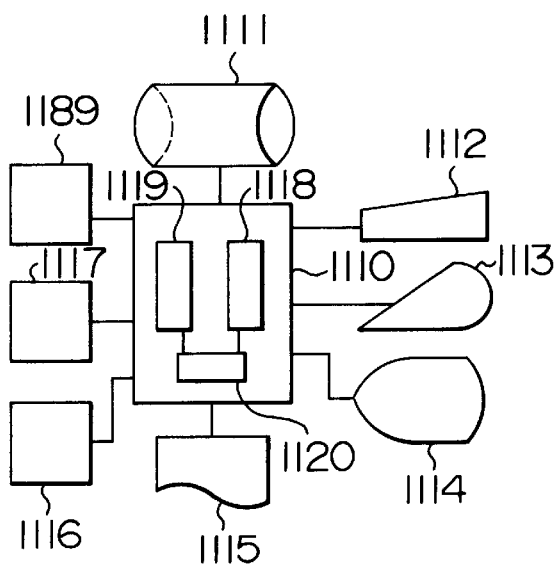
FIG. 56 is a diagram showing arrangement of a defects data analysis station.

The present embodiment is designed to include the visual inspection machine 4, the defect data analysis station 5, the probing tester 7, and the probing test data analysis station 8 in the inspection data analysis system described in the foregoing embodiment 1. The present embodiment is described with reference to FIG. 55. This embodiment substantially employs the arrangement of the system described in the foregoing embodiment 26, except that the visual inspection machine 4 and the defect data analysis station 5 are employed in place of the particle inspection machine 1 and the particle data analysis station 2. The visual inspection machine 4 is quite identical to the visual inspection machine 4 described in the foregoing embodiment 13. The defect data analysis station 5 includes the arrangement of the defect data analysis station 5 described in FIG. 37 as well as an external communication unit 1189 for communicating with the probing data analysis station 8 (see FIG. 56).

The data to be inputted in or outputted from the probing tester 7 is identical to that described in the foregoing embodiment 26. The defect database 1111 has the same arrangement of that described in FIG. 38.

Figures 7, 8, 9:
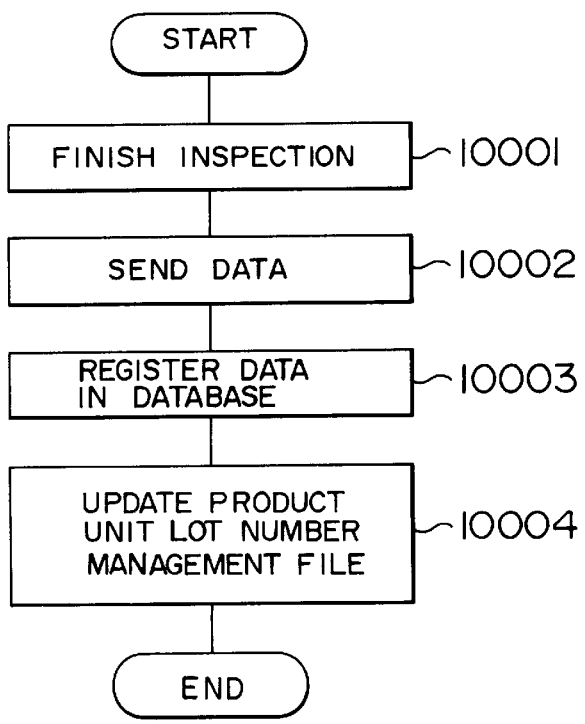
FIG. 7 is a chart showing arrangement of a map information file for each product.
FIG. 8 is a chart showing arrangement of a lot number managing file for each product.
FIG. 9 is a flowchart showing the procedure involved with registration of data.

The defect data processing unit 1110 includes the analysis data auxiliary file shown in FIG. 39, the map information file shown in FIG. 7, and the product unit wafer number management file, which is generally same as that shown in FIG. 8 except that if the product unit wafer number becomes zero, the data about the product kind is deleted from the analysis data auxiliary file.

Embodiment 33

The present embodiment concerns with an embodiment about how to use the defect data analysis station 5. It is generally same as how to use the defect data analysis station 5 described in the foregoing embodiment 14, except that the content of the analysis function icon has an additional analysis function described in the embodiments 34 to 37.

Embodiment 34

Next, the description will be directed to an embodiment about the analysis. This embodiment is referred to as defect yield correlation analysis.

The present embodiment is generally same as the foregoing embodiment 28. The embodiment 28 has been designed to analyze the particles using the inspection data analysis system described in the foregoing embodiments 26 and 27, while the present embodiment is designed to analyze the defects using the inspection data analysis system described in the foregoing embodiments 32 and 33.

Embodiment 35

Next, the description will be directed to an embodiment about the analysis. This embodiment is referred to as visual yield overlay trend.

The present embodiment is generally same as the foregoing embodiment 29. The embodiment 29 has been designed to analyze the particles using the particle probing test system described in the embodiments 23 and 27, while the present embodiment is designed to analyze the defects using the visual probing test system described in the foregoing embodiments 32 and 33. In FIG. 52, the right-hand axis of ordinate 1169 denotes a defect number, the left-hand axis of ordinate 1170 denotes a yield, and the axis of abscissa 1175 denotes a lot number and a wafer number.

Embodiment 36

Next, the description will be directed to an embodiment about the analysis. The embodiment is referred to as a yield for each kind of defects.

The present embodiment is generally same as the foregoing embodiment 30. The embodiment 30 has been designed to analyze the particles using the particle probing test system described in the foregoing embodiments 26 and 27, while the present embodiment is designed to analyze the defects using the visual probing test system described in the foregoing embodiments 32 and 33. The present embodiment treats the category of defects in palce of the category of a particle size described in the embodiment 30. In the present embodiment, as shown in FIG. 53, the axis of ordinate 1177 denotes a yield, the axis of abscissa 1176 denotes defect kinds, which are ranged in the order of pattern defects, particle defects, and the other defects.

Embodiment 37

Next, the description will be directed to an embodiment about the analysis. This embodiment is referred to as a yield for each defective process.

The present embodiment is generally same as the foregoing embodiment 31. The embodiment 31 has been designed to analyze the particles using the particle probing test system described in the foregoing embodiments 26 and 27, while the present embodiment is designed to analyze the defects using the visual probing test system described in the foregoing embodiments 32 and 33. In the present embodiment, as shown in FIG. 54, the axis of ordinate 1185 denotes the chip number and the axis of abscissa 1184 denotes the process name.

Embodiment 38

The present embodiment concerns with how to categorize the defects. The defects are categorized into a cause of defects, a defects-causing phenomenon, and a kind of defects. The cause of defects can be categorized into a resist residue, a fingerprint, a reticle, a pattern defect resulting from an reticle error, a pattern defect resulting from a resolution error, a discoloration defect resulting from over oxidation, and the other. The defects-causing phenomenon can be categorized into a pattern defect resulting from Al corrosion, a pattern defect resulting from a filled contact hole, a discoloration defect resulting from a pin hole, and the other. The kind of defects can be categorized into a pattern defect, a discoloration defect, a flaw, and the other. The defects are categorized in accordance with the foregoing categories in order to perform the data analysis described in each of the foregoing embodiments 15, 19, 20 or 36.

Embodiment 39

Figure 57:
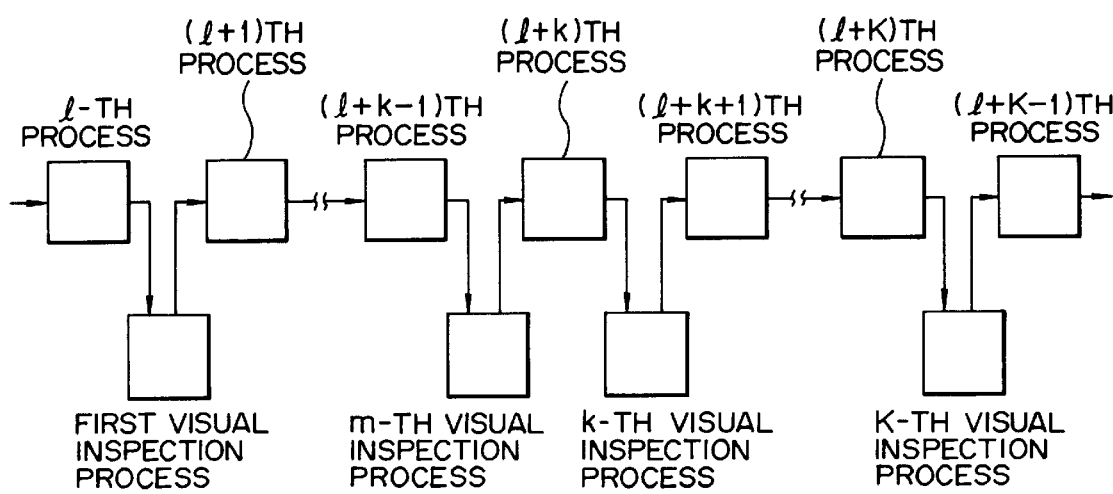
FIG. 57 is a diagram showing a relation between a particle inspection process and a visual inspection process.

The present embodiment concerns with a wafer manufacturing line on which the inventions described in the embodiments 26, 27 and 32, 33 are used with reference to FIG. 57. This wafer manufacturing line is designed to set particle inspection processes immediately after the manufacturing process on which the particles are often caused, the process on which the manufacturing machine is adjusted, and the like. And, it sets a management reference for a particle number per wafer to each particle inspection process. The particle data analysis station 2 serves to analyze the management reference particle inspection result in the manner described in the embodiment 9, monitor the change of the particle number on time in each particle inspection process, and pick up the process having a higher particle number than the management reference particle number. By the analysis described in the embodiment 10, the station 2 serves to pick up the process on which the sensed particle number is larger than that in any other process. After a m-th particle inspection process is picked up, the station 2 serves to select several manufacturing processes around the manufacturing process immediately before the m-th particle inspection process and set the visual inspection process immediately after the manufacturing process (see FIG. 57). The defects data analysis station 5 serves to analyze the visual inspection result in the manner described in the embodiments 15 to 25.

Embodiment 40

Figure 58:
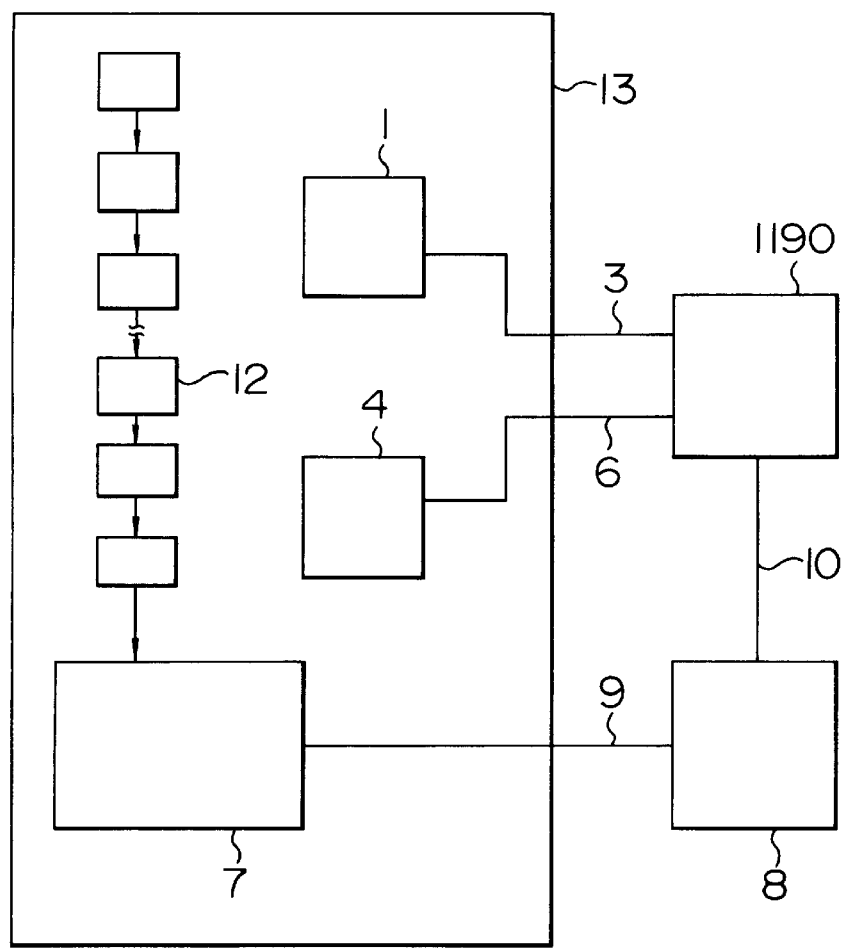
FIG. 58 is a diagram showing an overall system according to another embodiment of the present invention.
Figure 59:
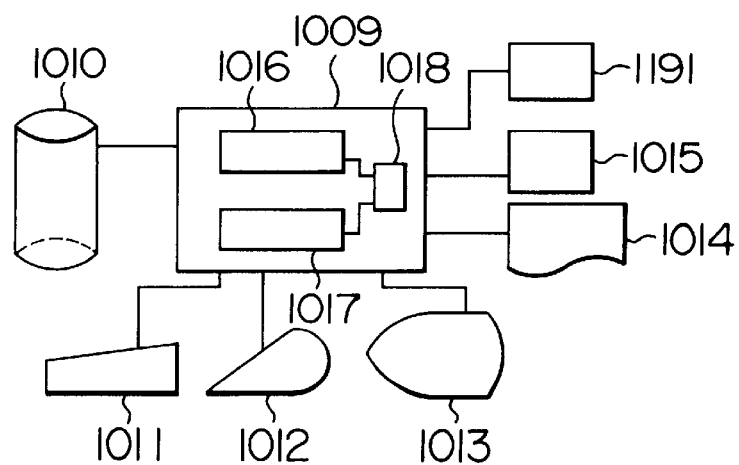
FIG. 59 is a diagram showing a data analysis station included in the system shown in FIG. 58.

The foregoing embodiment 1 has been designed to individually provide the particle data analysis station 2 and the defects data analysis station 5, though, the present embodiment is designed to integrate them into one workstation. The overall arrangement of the embodiment 1 will be illustrated in FIG. 58.

Figure 47:
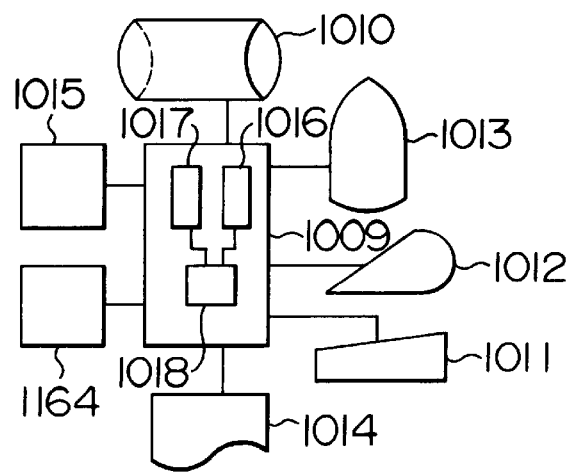
FIG. 47 is a diagram showing arrangement of the particle data analysis station.

The arrnagement of the component unit is equal to those shown in FIGS. 3, 36, 45, and 46, except that the data analysis station 1190 includes an external communication unit 1191 for communicating with the visual inspection machine 4 and the particle data analysis station 2 shown in FIG. 47.

Embodiment 41

Figure 60:
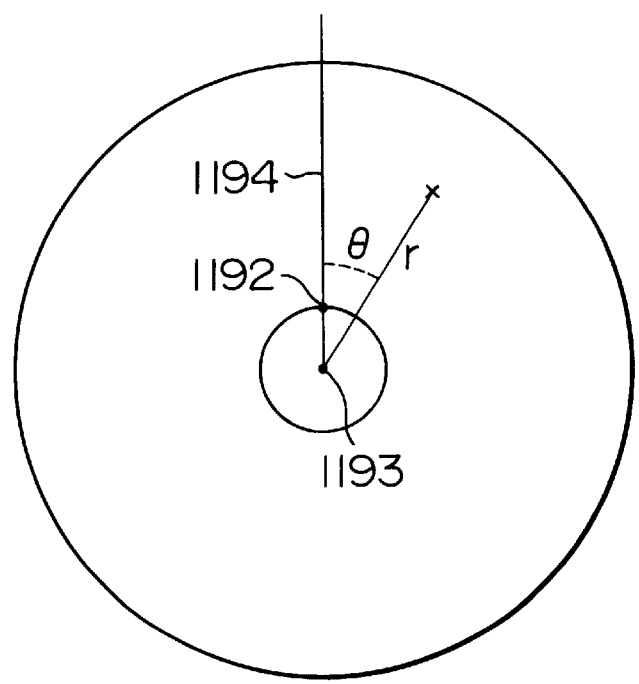
FIG. 60 is a view showing how to set a coordinate system when a magnetic disk is to be inspected.

The present embodiment concerns with a magnetic disk production line to which the present invention is applied. In the hardware arrangement shown in FIG. 1, the present embodiment employs a disk particle inspection machine in place of the particle inspection machine 1, a disk particle analysis station in place of the particle data analysis station 2, a disk visual inspection machine in place of the visual inspection machine 4, a disk defects analysis station in place of the defects data analysis station 5, a disk finished product inspection machine in place of the probing tester 7, and a disk product data analysis station in place of the probing data analysis station 8. The function of the inspection machine and the data analysis station is same as that described in the foregoing embodiments 2 to 37. Then, how to set location coordinates on a magnetic disk is described with reference to FIG. 60. On one part of the inner peripheral portion is attached a mark 1192 in the first magnetic disk manufacturing process. Assuming that the line connecting between a disk center 1193 and the mark is a reference line 1194, a two-dimensional polar coordinate system on a magnetic disk is set using the disk center and the reference line. Using the polar coordinate system, it is possible to carry out the functions such as the analysis, the operation, and the processing as described in each item of the embodiments 2 to 37 and 39. As an output form, nothing matching to the border 1055 of the semiconductor chip is output.

Embodiment 42

Figure 61:
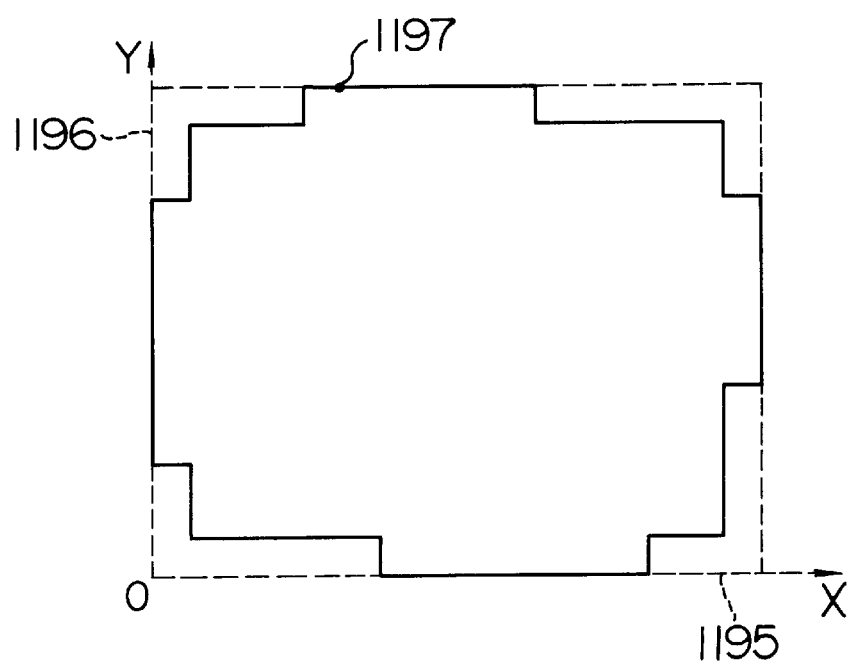
FIG. 61 is a view showing how to set a coordinate system when a circuit substrate is to be inspected.

The present embodiment concerns with a substrate production line to which the present invention is applied. In the hardware arrangement shown in FIG. 1, the present embodiment employs a substrate particle inspection machine in place of the particle inspection machine 1, a substrate particle analysis station in place of the particle data analysis station 2, a substrate visual inspection machine in place of the visual inspection machine 4, a substrate defects analysis station in place of the defects data analysis station 5, a substrate final inspection machine in place of the probing tester 7, and a substrate data analysis station in place of the probing data analysis station 8. The functions of the inspection machine and the data analysis station are basically same as those described in the embodiments 2 to 37. The present embodiment employs the steps of setting a minimum square enclosing a work as shown in FIG. 61, a mark 1197 on the work as a reference point, and an X-axis 1195 and a Y-axis 1196. Using this coordinate system, this embodiment serves to perform the analysis described in each item of the embodiments 3 to 37 and 39.

According to the present invention, it has been described that the relation between the defects and the product character is conventionally derived by taking the correlation between the defect density and the yield on a wafer basis. Since, however, the data can be analyzed on a chip basis, the present invention is capable of grasping the relation between the defects-causing condition of each chip and the product character of the chip, resulting in enabling new analysis of the data and elucidating the causal relation between the defects (cause) and the product character (result). This function makes contribution to providing effective decision materials for properly improving yields. Further, by individually using the particle inspection machine and the visual inspection machine, the inspection speeds of which are different, this invention has a new function of determining a process to be visually inspected in the mass production line from the particle inspection result. In addition, it has an advantage that it is unnecessary to match the particle inspection data to the defects inspection data in the overall process and machines.

The present invention is designed to formalize the operating method and the data retrieval routine in the analysis station and generalize the data analysis method. Hence, it is capable of easily knowing an abnormality-caused process and the content of the abnormality, so that a person in charge of the manufacturing machine can take rapid measures for the abnormality.

The present invention establishes a novel method for analyzing defects resulting from the product defect. This invention can be applied to the manufacturing line of a product (for example, a magnetic disk or a substrate) requiring the visual inspection and the final product inspection of the work.

What is claimed is:

1. An electronic device inspection system comprising:

first inspection means for inspecting defects on a work piece;

second inspection means for inspecting electric characteristics of at least a chip of the work piece;

first processing means for receiving and memorizing first information determined by the inspection performed by the first inspection means;

second processing means, separate from the first processing means, for receiving and memorizing second information determined by the inspection performed by the second inspection means; and communication means connected to the first processing means and the second processing means;

wherein a first analysis on the basis of the first information memorized by the first processing means and a second analysis on the basis of the second information memorized by the second processing means are processed separately in said first and second processing means, respectively, and wherein a third analysis on the basis of the first information and the second information is processed by one of the first and second processing means by transmitting at least one of the first information and the second information through the communication means from the other of the first and second processing means.

2. An electronic device inspection system as claimed in claim 1, wherein the first and second inspection means are disposed in a first area, the first area being controlled by a clean factor, and wherein the first and the second processing means are disposed outside of the first area.

3. An electronic device inspection system comprising:

a visual inspection means for inspecting defects on a work piece;

a particle inspection means for inspecting defects on the work piece;

a probing tester means for testing electric characteristics of at least a chip of the work piece;

a first processing means for receiving and memorizing first defect information determined by the inspection performed by the visual inspection means and second defect information determined by the inspection performed by the particle inspection means;

a second processing means, separate from the first processing means, for receiving and memorizing electric characteristic information determined by the probing tester means; and communication means connected to the first processing means and the second processing means;

wherein a first analysis on the basis of one of the first defect information and the second defect information and a second analysis on the basis of the electric characteristic information are processed separately in said first and second processing means, respectively, and wherein a third analysis on the basis of the electric characteristic information and one of the first defect information and the second defect information is processed by one of the first and second processing means by transmitting at least one of the electric characteristic information and one of the first defect information and the second-defect information through the communication means from the other of the first and second processing means.

4. An electronic device inspection system as claimed in claim 3, wherein the visual inspection means and the particle inspection means and the probing tester means are disposed in a first area, the first area being controlled by a clean factor, and wherein the first and the second processing means are disposed outside of the first area.

5. An electronic device inspection system comprising:

a first inspection means for inspecting defects on a work piece;

a second inspection means for inspecting electric characteristics of at least a chip of the work piece;

a first analysis unit comprising receiving means for receiving first information determined by the inspection performed by the first inspection means, and memory mean for memorizing the first information received by the receiving means, analysis means for analyzing the first information memorized by the memory means, and output means for outputting a result based on the analysis performed by the analysis means;

a second analysis unit, separate from the first analysis unit, comprising receiving means for receiving a second information determined by the inspection performed by the second inspection means, memory means for memorizing the second information received by the receiving means, analysis means for analyzing the second information memorized by the memory means, and output means for outputting a result based on the analysis performed by the analysis means; and a communication means for transmitting at least one of the first information and the second information between the first analysis unit and the second analysis unit.

6. An electronic device inspection system comprising:

a first device having a first processing means for processing first information based on inspected defects on a work piece and a first output means for outputting a result of the processed first information; and a second device having a second processing means, separate from the first processing means for processing second information based on inspected electrical characteristics of at least a chip of the work piece and a second output means for outputting a result of the processed second information; and communication means connected to the first device and the second device so as to output a processed result on the basis of the first information and the second information by at least one of the first outputting means and the second outputting means.

7. An electronic device inspection system comprising:

a first inspection machine to inspect defects on a work piece and to provide first information regarding the defects as an output;

a second inspection machine to inspect electric characteristics of at least a chip of the work piece and to provide second information regarding the electric characteristics as an output;

a first processor coupled to receive the first information from the first inspection machine;

a second processor, separate from the first processor, coupled to receive the second information from the second inspection machine; and a communication line connected to the first processor and the second processor;

wherein a first analysis on the basis of the first information received by the first processor and a second analysis on the basis of the second information received by the second processor are processed separately in said first and second processors, respectively, and wherein a third analysis on the basis of the first information and the second information is processed by one of the first and second processors by transmitting at least one of the first information and the second information through the communication line from the other of the first and second processors.

8. An electronic device inspection system as claimed in claim 7, wherein the first and second inspection machine are disposed in a first area, the first area being controlled by a clean factor, and wherein the first and the second processors are disposed outside of the first area.

9. An electronic device inspection system comprising:

a visual inspection machine to inspect defects on a work piece and to provide first defect information regarding the defects as an output;

a particle inspection machine to inspect defects on the work piece and to provide second defect information regarding the defects as an output;

a probing tester to test electric characteristics of at least a chip of the work piece and to provide electric characteristic information as an output;

a first processor coupled to receive the first defect information from the visual inspection machine and the second defect information from the particle inspection machine;

a second processor, separate from the first processor, coupled to receive the electric characteristic information determined from the probing tester; and a communication line connecting the first processor and the second processor;

wherein a first analysis on the basis of one of the first defect information and the second defect information and a second analysis on the basis of the electric characteristic information are processed separately in said first and second processors, respectively, and wherein a third analysis on the basis of the electric characteristic information and one of the first defect information and the second defect information is processed by one of the first and second processors by transmitting at least one of the electric characteristic information and one of the first defect information and the second defect information through the communication line from the other of the first and second processors.

10. An electronic device inspection system as claimed in claim 9, wherein the visual inspection machine and the particle inspection machine and the probing tester are disposed in a first area, the first area being controlled by a clean factor, and wherein the first and the second processors are disposed outside of the first area.

11. An electronic device inspection system comprising:

a first inspection machine to inspect defects on a work piece and to provide first information regarding the defects as an output;

a second inspection machine to inspect electric characteristics of at least a chip of the work piece and to provide second information regarding the electric characteristics as an output;

a first analysis unit comprising a receiver to receive first information determined by the inspection performed by the first inspection machine, a memory to memorize the first information received by the receiver, an analyzer for analyzing the first information memorized by the memory, and an output device to output a result based on the analysis performed by the analyzer;

a second analysis unit, separate from the first analysis unit, comprising a receiver to receive the second information determined by the inspection performed by the second inspection machine, a memory to memorize the second information received by the receiver, an analyzer to analyze the second information memorized by the memory, and an output device to output a result based on the analysis performed by the analyzer; and a communication line to transmit at least one of the first information and the second information between the first analysis unit and the second analysis unit.

12. An electronic device inspection system comprising:

a first device having a first processor to process first information based on inspected defects on a work piece and a first output device to output a result of the processed first information; and a second device having a second processor, separate from the first processor, to process second information based on inspected electrical characteristics of at least a chip of the work piece and a second output device to output a result of the processed second information; and a communication line connecting the first device and the second device so as to output a processed result on the basis of the first information and the second information by at least one of the first outputting device and the second outputting device.

13. An electronic device inspection method comprising:

inspecting defects on a work piece with a first inspection machine;

inspecting electric characteristics of at least a chip of the work-piece with a second inspection machine;

receiving and memorizing first information determined by the inspection performed by the first inspection machine using a first processor;

receiving and memorizing second information determined by the inspection performed by the second inspection means using a second processor, separate from the first processor, and communicating between the first processor and the second processor;

wherein a first analysis on the basis of the first information memorized by the first processor and a second analysis on the basis of the second information memorized by the second processor are processed separately in said first and second processors, respectively, and wherein a third analysis on the basis of the first information and the second information is processed by one of the first and second processors by transmitting at least one of the first information and the second information from the other of the first and second processors.

14. An electronic device inspection method as claimed in claim 13, further comprising:

displaying the first and second inspection machine in a first area, the first area being controlled by a clean factor, and disposing the first and the second processors outside of the first area.

* * * * *